(12) United States Patent
Yano et al.

(10) Patent No.: US 7,851,589 B2
(45) Date of Patent: Dec. 14, 2010

(54) POLYPEPTIDE DERIVED FROM THE RYANODINE RECEPTOR THAT INHIBITS CALCIUM LEAKAGE

(75) Inventors: Masafumi Yano, Ube (JP); Takeshi Yamamoto, Ube (JP); Masunori Matsuzaki, Ube (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 305 days.

(21) Appl. No.: 11/547,490

(22) PCT Filed: Mar. 29, 2005

(86) PCT No.: PCT/JP2005/005899

§ 371 (c)(1),
(2), (4) Date: Sep. 29, 2006

(87) PCT Pub. No.: WO2005/095452

PCT Pub. Date: Oct. 13, 2005

(65) Prior Publication Data

US 2008/0268489 A1  Oct. 30, 2008

(30) Foreign Application Priority Data

Mar. 31, 2004  (JP) ............................ 2004-102664

(51) Int. Cl.
*A61K 38/00* (2006.01)
(52) U.S. Cl. .................................................... 530/324
(58) Field of Classification Search ....................... None
See application file for complete search history.

(56) References Cited

FOREIGN PATENT DOCUMENTS

WO    2001/57188 A2 *  8/2001

OTHER PUBLICATIONS

"Introduction to Protein Structure," Branden and Tooze, Garland Publishing, Inc., New York, 1991, at p. 247.*
Lam et al., J. Biol. Chem. 270:26511-26522, 1995.*
Abaza et al., J. Prot. Chem. 11:433-444, 1992.*
Gausterer et al., Anti-Inflammatory and Anti-Allergy Agents in Medicinal Chem. 6:29-45, 2007.*
Dang et al., Clin Cancer Res 5:471-474, 1999.*
Fox, Nat Biotechnol 21:217, 2003.*
Juengst, BMJ 326:1410-1411, 2003.*
Yamamoto et al., Circulation 117:762-772, 2008.*
Takeshi Yamamoto, et al. "Postulated Role of Interdomain Interaction Within the Ryanodine Receptor in Ca2+ Channel Regulation", Journal of Biological Chemistry, XP 002427006, vol. 275, No. 16, Apr. 21, 2000, pp. 11618-11625.
Masafumi Yano, et al. "FKBP12.6-Mediated Stabilization of Calcium-Release Channel(Ryanodine Receptor) as a Novel Therapeutic Strategy Against Heart Failure", Circulation, American Heart Association, XP002990501, vol. 107, No. 3. Jan. 2003, pp. 477-484.

Takeshi Yamamoto, et al. "Interruption of Specific Domain-Domain Interaction Within Ryanodine Receptor Mediates Stabilization of Ryanodine Receptor in Failing Hearts", Circulation, XP 009081455, vol. 114, No. 18, Oct. 31, 2006, 2 Pages.
Tunwell, Richard E. A. et al., "The Human Cardiac Muscle Ryanodine Receptor-calcium Release Channel: Identification, Primary Structure and Topological Analysis" Biochem J., vol. 318, pp. 477-487, 1996.
Lui, Zheng et al.,"Three-dimensional Reconstruction of the Recombinant Type 2 Ryanodine Receptor and Localization of Its Divergent Region 1", The Jurnal of Biological Chemistry, vol. 277, No. 48, pp. 46712-46719,2002.
D.J. Beuckelmann, et al., "Intracellular calcium handling in isolated ventricular myocytes from patients with terminal heart failure", Circulation Journal of the American Heart Association, 85, 1046-1055 (1992).
J.K. Gwathmey, et al., "Abnormal intracellular calcium handling in myocardium from patients with end-stage heart failure", Circular Research Journal of the American Heart Association, 61, 70-76 (1987).
Debra L. Baker, et al., "Targeted Overexpression of the Sarcoplasmic Reticulum $Ca^{2+}$-ATPase Increases Cardiac Contractility in Transgenic Mouse Hearts", Circulation Research Journal of the American Heart Association, 83, 1205-1214 (1998).
Götz Münch, et al., "Unchanged protein expression of sarcoplasmic reticulum $Ca^{2+}$-ATPase, phospholamban, and calsequestrin in terminally failing human myocardium", J Mol Med, 76, 434-441 (1998).
Steven O. Marx, et al., "PKA Phosphorylation Dissociates FKBP12.6 from the Calcium Release Channel (Ryanodine Receptor): Defective Regulation in Failing Hearts", Cell, 101, 365-376 (2000).
Andrew R. Marks, "Clinical Implications of Cardiac Ryanodine Receptor/Calcium Release Channel Mutations Linked to Sudden Cardiac Death", Circulation Journal of the American Heart Association, 106, 8-10 (2002).
Xander H.T. Wehrens, et al., "FKBP12.6 Deficiency and Defective Calcium Release Channel (Ryanodine Receptor) Function Linked to Exercise-Induced Sudden Cardiac Death", Cell, 113, 829-840 (2003).
Masafumi Yano, et al., "Altered Stoichiometry of FKBP12.6 Versus Ryanodine Receptor as a Cause of Abnormal $Ca^{2+}$ Leak Through Ryanodine Receptor in Heart Failure", Circulation Journal of the American Heart Association, 102, 2131-2136 (2000).

* cited by examiner

*Primary Examiner*—David J Steadman
(74) *Attorney, Agent, or Firm*—Oblon, Spivak, McClelland, Maier & Neustadt, L.L.P.

(57) ABSTRACT

A polypeptide exhibiting the effect of inhibiting $Ca^{2+}$ leakage in a target cell, the polypeptide having the amino acid sequence of any of SEQ ID NOs: 3 to 9 or an amino acid sequence obtained through deletion, insertion, substitution, or addition of one or more amino acids in the aforementioned amino acid sequence; a polynucleotide encoding the polypeptide; and a pharmaceutical composition containing, as an active ingredient, the polypeptide or an expression product of the polynucleotide.

1 Claim, 5 Drawing Sheets

POLYPEPTIDE DERIVED FROM THE RYANODINE RECEPTOR THAT INHIBITS CALCIUM LEAKAGE

TECHNICAL FIELD

The present invention relates to a polypeptide exhibiting the effect of inhibiting $Ca^{2+}$ leakage (hereinafter may be referred to as the "$Ca^{2+}$ leakage inhibitory effect") in the endoplasmic reticulum of a target cell, and to a pharmaceutical composition containing the polypeptide as an active ingredient. The present invention also relates to a screening method for selecting a compound exhibiting an activity of enhancing or suppressing the $Ca^{2+}$ leakage inhibitory effect against $Ca^{2+}$ leakage induction in the endoplasmic reticulum of a target cell.

BACKGROUND ART $Ca^{2+}$ flux in myocardial cells is an important factor for myocardial contraction. In recent years, many reports have shown that abnormal $Ca^{2+}$ regulation (abnormal calcium handling) in myocardial cells is closely related to onset of heart failure (see Non-Patent Documents 1 and 2). In general, $Ca^{2+}$ flux in a myocardial cell is as follows. A myocardial cell contains sarcoplasmic reticulum serving as a $Ca^{2+}$ pool, and influx of extracellular $Ca^{2+}$ triggers $Ca^{2+}$ release from the sarcoplasmic reticulum via ryanodine receptor (RyR) into the cytoplasm. This increases cytoplasmic $Ca^{2+}$ concentration, resulting in myocardial contraction. Meanwhile, myocardial dilation requires a decrease in cytoplasmic $Ca^{2+}$ concentration, which is attained through $Ca^{2+}$ reuptake into the sarcoplasmic reticulum by means of sarco(endo)plasmic reticulum Ca-ATPase (SERCA). Excess $Ca^{2+}$ which has been initially taken up from the outside of the cell is discharged to the outside thereof by means of $Na^+$—$Ca^{2+}$ exchange pump (NCX). Recent studies have focused on the sarcoplasmic reticulum, which serves as a $Ca^{2+}$ pool in a myocardial cell, in view that the sarcoplasmic reticulum is related to abnormal calcium handling, and depletion of $Ca^{2+}$ in the sarcoplasmic reticulum has been shown in the case of heart failure. Therefore, it may be possible to develop an anti-heart failure drug or an antiarrhythmic drug on the basis of a new concept of targeting an increase in $Ca^{2+}$ concentration in the sarcoplasmic reticulum to a normal level.

Conventionally, studies on a mechanism of abnormal calcium handling have focused on lowering SERCA activity. In practice, overexpression of SERCA has shown to improve cardiac contraction performance and cardiac relaxation performance (see Non-Patent Document 3). However, heart failure patients do not necessarily exhibit a change in SERCA amount or SERCA activity (see Non-Patent Document 4). Therefore, in recent years, studies have focused on involvement of RyR, in addition to SERCA, in the abnormal calcium handling mechanism.

RyR is a protein which binds specifically to ryanodine, which is an ergot alkaloid. RyR has a tetrameric structure containing subunits of about 5,000 amino acids, and is considered to form a foot structure on the N-terminal side and a channel on the C-terminal side. RyR is classified into three subtypes; i.e., RyR1, which is localized in skeletal muscle and the brain (in particular, the cerebellum); RyR2, which is localized in myocardium, smooth muscle, and the brain (entire brain); and RyR3, which is present in the brain (in particular, the hippocampus and thalamus), smooth muscle, and skeletal muscle. In the present invention, the ryanodine receptor encompasses all these subtypes, but is preferably RyR2.

As described above, RyR2 is a homotetramer containing four subunits of about 5,000 amino acids, in which one subunit is bound to one molecule of FK506-binding protein 12.6 (FKBP12.6). Conceivably, when RyR2 is bound to FKBP12.6, the structure of RyR2 is stabilized, whereas when FKBP12.6 is dissociated from RyR2, $Ca^{2+}$ is released from the sarcoplasmic reticulum to the cytoplasm.

As has been known, FKBP12.6 is dissociated from RyR2 through phosphorylation with protein kinase A (PKA). In heart failure patients, hyperphosphorylation with PKA causes dissociation of FKBP12.6 (60% or more), which results in enhancement of $Ca^{2+}$ sensitivity of RyR2, leading to abnormal leakage of $Ca^{2+}$ from the sarcoplasmic reticulum (see Non-Patent Document 5).

RyR2 mutation has been observed in several heart-related diseases [CPVT (catecholaminergic polymorphic ventricular tachycardia), FPVT (familial polymorphic ventricular tachycardia), and ARVD (arrhythmogenic right ventricular dysplasia)] (see Non-Patent Document 6). In practice, in vitro studies have shown that CPVT-related RyR2 mutation reduces the affinity of RyR2 to FKBP12.6, and enhances the sensitivity of RyR2 to phosphorylation (see Non-Patent Document 7).

In addition, experiments employing the sarcoplasmic reticulum of the left ventricular myocardium of a dog model with heart failure induced by high-frequency right ventricular pacing have shown that abnormal $Ca^{2+}$ leakage via RyR2, which is observed in the heart failure model, is attributed to a change in RyR2 structure associated with reduction of the stoichiometric composition of FKBP12.6 (see Non-Patent Document 8).

Recent studies have shown that JTV519, which is a 1,4-benzothiazepine derivative, corrects abnormal $Ca^{2+}$ leakage via RyR2 (see Non-Patent Document 9). JTV519 was developed as a therapeutic drug for ischemic disorders, and was subjected to clinical tests. According to Yano, M., et al., RyR2 is an effective target of JTV519, and a drug may be developed on the basis of a new concept of correcting calcium handling through the RyR2-stabilizing effect of JTV519.

In view of the foregoing, in the art, demand has arisen for development of a substance exhibiting the effect similar to that of JTV519 (i.e., RyR2-stabilizing effect), and exhibiting no side effects.

Non-Patent Document 1: Beuckelmann, et al., Circulation, 85, 1046-1055 (1992)
Non-Patent Document 2: Gwathmey, et al., Circ Res, 61, 70-76 (1987)
Non-Patent Document 3: Baker, et al., Circ Res, 83, 1205-1214 (1998)
Non-Patent Document 4: Munch, et al., J Mol Med, 76, 434-441 (1998)
Non-Patent Document 5: Marx, et al., Cell, 101, 365-376 (2000)
Non-Patent Document 6: Marks, Circulation, 106, 8-10 (2002)
Non-Patent Document 7: Wehrens, et al., Cell, 113, 829-840 (2003)
Non-Patent Document 8: Yano, et al., Circulation, 102, 2131-2136 (2000)
Non-Patent Document 9: Yano, et al., Circulation, 107, 477-484 (2003)

DISCLOSURE OF THE INVENTION

As described above, if there was provided a new substance which improves myocardial performance through improvement or inhibition of abnormal calcium handling (e.g., $Ca^{2+}$ leakage induction in myocardial sarcoplasmic reticulum), the substance would be useful for elucidation of calcium handling regulation mechanism in myocardial endoplasmic reticulum, elucidation of heart failure mechanism, or improvement of abnormal $Ca^{2+}$ leakage regulation in endoplasmic reticulum.

If there was provided a polypeptide exhibiting $Ca^{2+}$ leakage inhibitory effect, or an expression product of a polynucleotide (hereinafter may be referred to as a "polynucleotide expression product") exhibiting $Ca^{2+}$ leakage inhibitory effect, the polypeptide or the polynucleotide expression product would be expected as a therapeutic or preventive agent for, for example, diseases associated with abnormal intracellular calcium regulation (abnormal intracellular calcium handling), such as heart failure, cardiomyopathy, valvulopathy, ischemic heart disease, myocardial infarction, angina pectoris, arrhythmia, hypertension, peripheral circulatory disorder, diabetes, dysmnesia, cerebral infarction, and malignant hyperthermia. In addition, the polypeptide or the polynucleotide expression product could be employed for selecting, through screening, a candidate compound which promotes or suppresses the $Ca^{2+}$ leakage inhibitory effect in the endoplasmic reticulum of a cell.

Therefore, the present invention contemplates provision of a polypeptide exhibiting the effect of inhibiting $Ca^{2+}$ leakage in the endoplasmic reticulum of a target cell; a polynucleotide expression product exhibiting such $Ca^{2+}$ leakage inhibitory effect; a pharmaceutical composition containing, as an active ingredient, the polypeptide or the polynucleotide expression product; and a screening method for selecting a compound exhibiting an activity of enhancing or suppressing the $Ca^{2+}$ leakage inhibitory effect in the endoplasmic reticulum of a target cell, the method employing the polypeptide or the polynucleotide expression product.

In view of the foregoing, for the purpose of searching for a new substance exhibiting the $Ca^{2+}$ leakage inhibitory effect in endoplasmic reticulum, firstly, the present inventors have searched for, as a therapeutic peptide which is considered to correct abnormality in RyR2 structure, a polypeptide exhibiting the $Ca^{2+}$ leakage inhibitory effect in endoplasmic reticulum. As a result, the present inventors have newly found that a polypeptide having a sequence of amino acids corresponding to positions 2114 to 2149 of the amino acid sequence of RyR2 exhibits the $Ca^{2+}$ leakage inhibitory effect in endoplasmic reticulum. Furthermore, on the basis of the aforementioned sequence of amino acids, the present inventors have prepared polypeptides having amino acid sequences of different lengths, and have found that some polypeptides of the thus-prepared polypeptides exhibit the $Ca^{2+}$ leakage inhibitory effect. The present invention has been accomplished on the basis of these findings.

Accordingly, the present invention provides a polypeptide which is selected from the group consisting of polypeptides described below in (a) and (b):
(a) a polypeptide having the amino acid sequence of any of SEQ ID NOs: 3 to 9; and
(b) a polypeptide having an amino acid sequence obtained through deletion, insertion, substitution, or addition of one or more amino acids in the amino acid sequence of any of SEQ ID NOs: 3 to 9, and which exhibits the effect of inhibiting $Ca^{2+}$ leakage in a target cell.

The present invention also provides a polynucleotide selected from the group consisting of polynucleotides described below in (c), (d), and (e):
(c) a polynucleotide encoding a polypeptide having the amino acid sequence of any of SEQ ID NOs: 3 to 9;
(d) a polynucleotide which can be hybridized with the polynucleotide described in (c) above under stringent conditions, and which can produce a corresponding expression product; and
(e) a polynucleotide which has a DNA sequence 80% or more homologous to the polynucleotide described in (c) above, and which can produce a corresponding expression product, an expression product of the polynucleotide exhibiting the effect of inhibiting $Ca^{2+}$ leakage in a target cell.

The present invention also provides a pharmaceutical composition containing, as an active ingredient, the aforementioned polypeptide or an expression product of the aforementioned polynucleotide.

The present invention also provides a screening method for selecting an agonist or an antagonist with respect to the $Ca^{2+}$ leakage inhibitory effect in the endoplasmic reticulum of a target cell, which method is characterized by comprising measuring, in the presence or absence of a test substance, the level of the $Ca^{2+}$ leakage inhibitory effect of the aforementioned polypeptide in the endoplasmic reticulum of a target cell; and comparing the level measured in the presence of the test substance with the level measured in the absence of the test substance, to thereby select the test substance as an agonist which enhances the inhibitory effect or as an antagonist which suppresses the inhibitory effect.

The present invention also provides a screening method for selecting an agonist or an antagonist with respect to the $Ca^{2+}$ leakage inhibitory effect in the endoplasmic reticulum of a target cell, which method is characterized by comprising measuring, in the presence or absence of a test substance, the level of the $Ca^{2+}$ leakage inhibitory effect of an expression product of the aforementioned polynucleotide in the endoplasmic reticulum of a target cell; and comparing the level measured in the presence of the test substance with the level measured in the absence of the test substance, to thereby select the test substance as an agonist which enhances the inhibitory effect or as an antagonist which suppresses the inhibitory effect.

The present invention also provides a screening method for selecting a candidate substance which enhances the $Ca^{2+}$ leakage inhibitory effect of the aforementioned polypeptide in the endoplasmic reticulum of a target cell, which method comprises the following steps (1) to (5):
(1) a step of providing a target cell transformed with an expression vector containing a polynucleotide encoding the aforementioned polypeptide;
(2) a step of adding FK506 to the endoplasmic reticulum of the target cell so as to induce $Ca^{2+}$ leakage in the presence or absence of a test substance;
(3) a step of measuring, by means of a $Ca^{2+}$ indicator, the amount of $Ca^{2+}$ leaked from the endoplasmic reticulum of the target cell, to thereby determine the amount of change in $Ca^{2+}$ leakage from the endoplasmic reticulum in the presence or absence of the test substance;
(4) a step of adding FK506 to the endoplasmic reticulum of a non-transformed cell so as to induce $Ca^{2+}$ leakage in the absence of the test substance, measuring by means of a $Ca^{2+}$ indicator the amount of $Ca^{2+}$ having leaked from the endoplasmic reticulum, and determining the difference between the amount of $Ca^{2+}$ as measured outside the endoplasmic reticulum; i.e., the standard amount, and each of the amounts as determined in (3) above in the presence and absence of the test substance; and
(5) a step of selecting the test substance as a candidate substance when the difference between the standard amount and the amount as determined in the presence of the test substance is smaller than the difference between the standard amount and the amount as determined in the absence of the test substance.

The present invention also provides a screening method for selecting a candidate substance which enhances the $Ca^{2+}$ leakage inhibitory effect of an expression product of the aforementioned polynucleotide in the endoplasmic reticulum of a target cell, which method comprises the following steps (1) to (5):

(1) a step of providing a target cell transformed with an expression vector containing the aforementioned polynucleotide;
(2) a step of adding FK506 to the endoplasmic reticulum of the target cell so as to induce $Ca^{2+}$ leakage in the presence or absence of a test substance;
(3) a step of measuring, through RT-PCR, the amount of expression of the polynucleotide in the endoplasmic reticulum of the target cell in the presence or absence of the test substance;
(4) a step of comparing the expression amount in the presence of the test substance with the expression amount in the absence of the test substance; and
(5) a step of selecting the test substance as a candidate substance when the expression amount in the presence of the test substance is greater than the expression amount in the absence of the test substance.

The present invention also provides a screening method for selecting a candidate substance which enhances the $Ca^{2+}$ leakage inhibitory effect of the aforementioned polypeptide in a target cell, which method comprises the following steps (1) to (5):

(1) a step of providing a target cell transformed with an expression vector containing a polynucleotide encoding the aforementioned polypeptide;
(2) a step of adding FK506 to the endoplasmic reticulum of the target cell so as to induce $Ca^{2+}$ leakage in the presence or absence of a test substance;
(3) a step of measuring, by means of an antibody against the polypeptide, the amount of the polypeptide produced in the target cell in the presence or absence of the test substance;
(4) a step of comparing the production amount in the presence of the test substance with the production amount in the absence of the test substance; and
(5) a step of selecting the test substance as a candidate substance when the production amount in the presence of the test substance is greater than the production amount in the absence of the test substance.

The present invention also provides a screening kit for selecting an agonist or an antagonist with respect to the $Ca^{2+}$ leakage inhibitory effect of the aforementioned polypeptide or an expression product of the aforementioned polynucleotide in the endoplasmic reticulum of a target cell, which kit is characterized by comprising at least one species selected from the group consisting of the polypeptide and the expression product, which are contained in the target cell, and FK506.

The polypeptide of the present invention exhibits the effect of inhibiting $Ca^{2+}$ leakage in the endoplasmic reticulum of a target cell, and therefore is useful as a therapeutic or preventive agent for, for example, diseases associated with abnormal intracellular calcium handling. The polypeptide can be employed for selecting, through screening, a compound exhibiting an activity of enhancing or suppressing the $Ca^{2+}$ leakage inhibitory effect in the endoplasmic reticulum of a target cell.

BEST MODE FOR CARRYING OUT THE INVENTION

[Definition]

Figure 1:
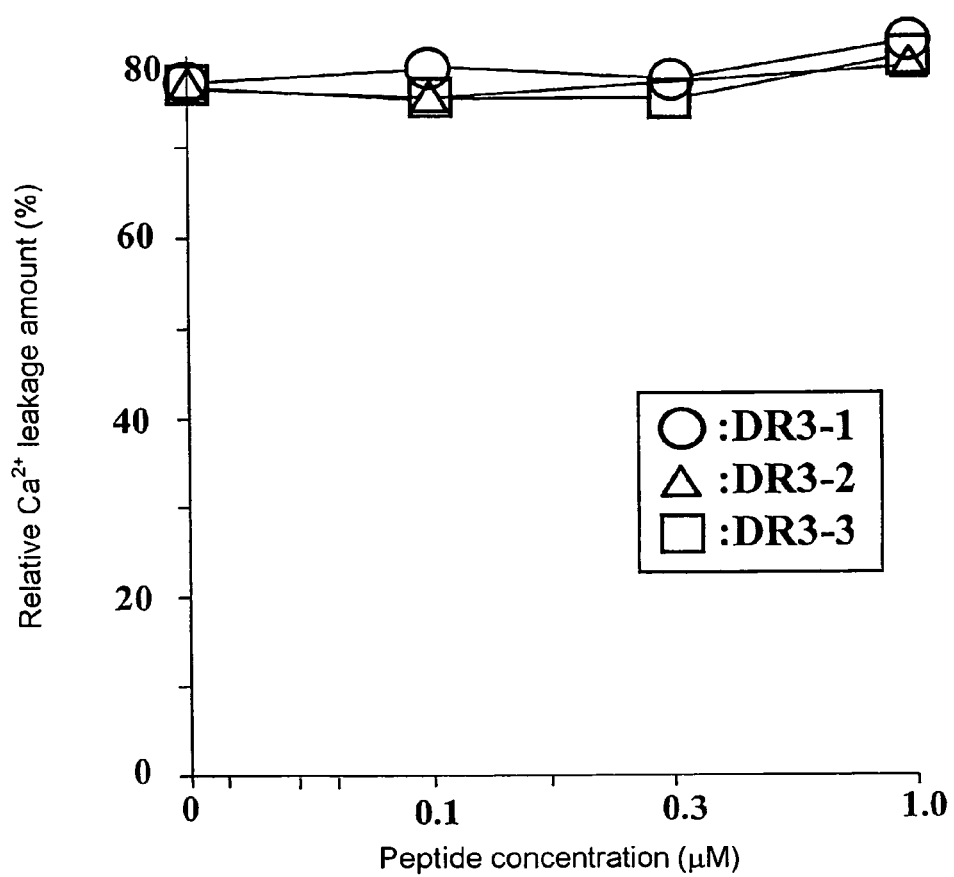
FIG. 1 shows the effects of synthesized polypeptides on FK506-induced $Ca^{2+}$ leakage in the sarcoplasmic reticulum derived from canine myocardium.

As used herein, abbreviations of amino acids, peptides, nucleotide sequences, nucleic acids, etc. are according to IUPAC-IUB nomenclature [IUPAC-IUB Communication on Biological Nomenclature, Eur. J. Biochem., 138: 9 (1984)], "Guideline for preparation of a specification, etc. including nucleotide sequences or amino acid sequences" (edited by Japan Patent Office), and conventional symbols used in the art.

As used herein, the term "gene" encompasses double-stranded DNA, as well as single-stranded DNA (sense strand or antisense strand) constituting the double-stranded DNA. No limitation is imposed on the length of such DNA. Therefore, unless otherwise specified, the polynucleotide (DNA molecule) encoding the polypeptide of the present invention encompasses double-stranded DNA including human genomic DNA, single-stranded DNA (sense strand) including cDNA, single-stranded DNA (antisense strand) having a sequence complementary to the sense strand, synthetic DNA, and fragments thereof.

As used herein, "gene (DNA molecule)" may include any functional region; for example, at least one of an expression inhibitory region, a coding region, a leader sequence, an exon, and an intron. The term "polynucleotide" encompasses RNA and DNA. The term "DNA molecule" encompasses cDNA, genomic DNA, and synthetic DNA. The polypeptide having a specific amino acid sequence, or the polynucleotide encoding the polypeptide encompasses its fragments, homologues, derivatives, and mutants.

Examples of mutants of the polynucleotide (mutant DNA) include naturally occurring allelic mutants; non-naturally occurring mutants; and mutants obtained through deletion, substitution, addition, or insertion. Note that such a mutant encodes a polypeptide having substantially the same function as the polypeptide encoded by the non-mutated polynucleotide.

Variation of the polypeptide (modification of amino acid sequence) does not necessarily naturally occur through, for example, mutation or post-translational modification, and may be artificially performed by use of a naturally occurring gene (e.g., a fragment of the ryanodine receptor gene according to the present invention). Examples of mutants of the aforementioned polypeptide include allelic mutants, homologues, and naturally occurring mutants, which are at least 80% (preferably 95%, more preferably 99%) homologous to the non-mutated polypeptide.

The mutant DNA is conservative, or silent with respect to the amino acid sequence encoded by the DNA (i.e., no change occurs in amino acid residues encoded by the mutated nucleic acid sequence). Examples of conservative amino acid substitutions are as follows.

| Original amino acid residue | Conservatively substituted amino acid residue |
|---|---|
| Ala | Ser |
| Arg | Lys |
| Asn | Gln or His |
| Asp | Glu |
| Cys | Ser |
| Gln | Asn |
| Glu | Asp |
| Gly | Pro |
| His | Asn or Gln |
| Ile | Leu or Val |
| Leu | Ile or Val |
| Lys | Arg, Asn, or Glu |
| Met | Leu or Ile |
| Phe | Met, Leu, or Tyr |
| Ser | Thr |
| Thr | Ser |
| Trp | Tyr |
| Tyr | Trp or Phe |
| Val | Ile or Leu |

In general, one or more codons encoding a Cys residue affect the disulfide bonds of a specific polypeptide.

Amino acid residue substitutions which are generally considered to change protein properties are, for example, the following substitutions:

a) substitution of a hydrophobic residue with a hydrophilic residue; for example, substitution of Leu, Ile, Phe, Val, or Ala with Ser or Thr;

b) substitution of an amino acid residue other than Cys and Pro with Cys or Pro;

c) substitution of a residue having an electrically positive side chain (e.g., Lys, Arg, or His) with an electrically negative residue (e.g., Glu or Asp); and d) substitution of an amino acid residue having a very large side chain (e.g., Phe) with an amino acid residue having no side chain (e.g., Gly).

[1] Polypeptide of the Present Invention

The polypeptide of the present invention (and the polypeptide employed in the screening method of the present invention; hereinafter may be referred to simply as "the invention polypeptide") is any of the following polypeptides (a) and (b):

(a) a polypeptide having the amino acid sequence of any of SEQ ID NOs: 3 to 9; and (b) a homologue of the aforementioned polypeptide; i.e., a polypeptide having an amino acid sequence obtained through deletion, insertion, substitution, or addition of one or more amino acids in the amino acid sequence of any of SEQ ID NOs: 3 to 9. The invention polypeptide exhibits the effect of inhibiting $Ca^{2+}$ leakage in a target cell.

The polypeptide represented by SEQ ID NO: 3, which is named "R2P," has a sequence of 36 amino acids corresponding to positions 2114 to 2149 of the amino acid sequence of human ryanodine receptor type 2 (hRyR2). SEQ ID NO: 20 represents the DNA sequence encoding the amino acid sequence of R2P. As shown in SEQ ID NO: 2, the DNA encoding the aforementioned ryanodine receptor type 2 contains 14,901 bases. As shown in SEQ ID NO: 1, the amino acid sequence encoded by the DNA contains 4,967 amino acids (Genbank Accession No. NM 001035).

The polypeptide represented by SEQ ID NO: 4 is MSV-R2P (M+2112-2149), which is obtained through addition of three amino acids (methionine, serine, and valine) to the N-terminal of R2P (SEQ ID NO: 3). The polypeptide represented by SEQ ID NO: 5 is RP1-30 (2114-2143), which is obtained through deletion of six amino acids at the C-terminal of R2P. The polypeptide represented by SEQ ID NO: 6 is RP1-25 (2114-2138), which is obtained through deletion of 11 amino acids at the C-terminal of R2P. The polypeptide represented by SEQ ID NO: 7 is RP1-20 (2114-2133), which is obtained through deletion of 16 amino acids at the C-terminal of R2P. The polypeptide represented by SEQ ID NO: 8 is RP13-32 (2126-2145), which is obtained through deletion of 12 amino acids at the N-terminal of R2P and deletion of four amino acids at the C-terminal thereof. The polypeptide represented by SEQ ID NO: 9 is RP17-36 (2130-2149), which is obtained through deletion of 16 amino acids at the N-terminal of R2P. The DNA sequences encoding these polypeptides are represented by SEQ ID NOs: 21 to 26.

No particular limitation is imposed on the number and position of amino acids which undergo modification (i.e., deletion, insertion, substitution, or addition) in the amino acid sequence of any of SEQ ID NOs: 3 to 9 shown in (b) above, so long as the polypeptide having the thus-modified amino acid sequence exhibits substantially the same activity as the polypeptide having the amino acid sequence of any of SEQ ID NOs: 3 to 9 (in particular, R2P having the amino acid sequence of SEQ ID NO: 3); i.e., these polypeptides exhibit the same effect. Preferably, one to a plurality of amino acids undergo the aforementioned modification. However, as described below in Example, the polypeptides represented by SEQ ID NOs: 4 to 9 also exhibit $Ca^{2+}$ leakage inhibitory activity. Therefore, as used herein, the expression "modification of a plurality of amino acids in R2P" refers to the case where 2 to 20 amino acids of the amino acid sequence of R2P undergo deletion, insertion, substitution, or addition. This amino acid modification is preferably performed such that homology in the corresponding amino acids between the thus-modified polypeptide and the polypeptide represented by SEQ ID NO: 3 is, for example, about 80% or more, more preferably about 95% or more, particularly preferably about 98% or more.

Polypeptide or polynucleotide homology can be analyzed through measurement employing sequence analysis software (e.g., FASTA program) (Clustal, V., Methods Mol. Biol., 25, 307-318 (1994)). In the most preferred and convenient method for homology analysis, for example, a sequence is stored in a computer-readable medium (e.g., flexible disk, CD-ROM, hard disk drive, external disk drive, or DVD), and subsequently, by use of the thus-stored sequence, known sequence databases are searched through well known search means. Specific examples of such known sequence databases include the following databases:

DNA Database of Japan (DDBJ);

Genebank; and the European Molecular Biology Laboratory Nucleic Acid Sequence Database (EMBL).

Homology analysis can employ numerous search algorithms. An example of such search algorithms is a program called "BLAST." This BLAST program includes five BLAST means. Three of the five means (BLASTN, BLASTX, and TBLASTX) are designed for nucleotide sequence query, and the remaining two means (BLASTP and TBLASTN) are designed for protein sequence query (Coulson, Trends in Biotechnology, 12: 76-80 (1994); Birren, et al., Genome Analysis, 1: 543-559 (1997)).

Furthermore, an additional program (e.g., a sequence alignment program or a program for identifying a remote sequence) can be employed for analysis of an identified sequence in the art.

The invention polypeptide may be, for example, a polypeptide derived from human cell, in particular, human myocardial cell, smooth muscle cell, skeletal muscle cell, brain neuron, neuroblast, or pancreatic β cell; or a polypeptide derived from human tissue, in particular, human heart, arterial/venous vessel, skeletal muscle, smooth muscle, cerebrum (cerebral cortex), cerebellum, pancreas, or the like. Alternatively, the invention polypeptide may be prepared through chemical synthesis on the basis of the amino acid sequence data of such a human-derived polypeptide. Examples of the homologue of the invention polypeptide (a) described in (b) above include proteins which exhibit $Ca^{2+}$ leakage inhibitory activity and are derived from yeast, nematode, plant tissue, or mammal other than human. Examples of the mammal include horse, sheep, cattle, dog, monkey, cat, bear, mouse, rat, and rabbit.

The aforementioned $Ca^{2+}$ leakage inhibitory effect of the invention polypeptide in a target cell is more specifically the effect of inhibiting intracellular calcium increase induced by $Ca^{2+}$ leakage in the endoplasmic reticulum of the cell, and increasing $Ca^{2+}$ uptake into the endoplasmic reticulum, to thereby inhibit $Ca^{2+}$ leakage and to improve abnormal intracellular calcium handling (regulation). Examples of the aforementioned cell endoplasmic reticulum include sarcoplasmic reticulum. Specific examples of the sarcoplasmic reticulum include sarcoplasmic reticulum prepared from normal or failing myocardium, sarcoplasmic reticulum prepared from vascular smooth muscle, and sarcoplasmic reticulum prepared from skeletal muscle. In, for example, myocardial tissue, the $Ca^{2+}$ leakage inhibitory effect is expected to result in an increase in myocardial contractile force, leading to improvement of heart failure or arrhythmia.

The $Ca^{2+}$ leakage inhibitory effect can also be regarded as the effect of stabilizing ryanodine receptor function. Specifically, the ryanodine receptor function stabilizing effect refers to the effect of maintaining ryanodine receptor function in a normal state (i.e., in a state of normal tissues or normal cells of a healthy individual). As used herein, the ryanodine receptor function can also be regarded as the function of inhibiting (suppressing) $Ca^{2+}$ leakage and regulating the transmission of $Ca^{2+}$ signals from the sarcoplasmic reticulum, so as to maintain the amount of $Ca^{2+}$ stored in the sarcoplasmic reticulum. Therefore, "maintaining ryanodine receptor function" refers to maintaining the state where physiological stimulation (e.g., membrane potential change) induces opening/closing of the ryanodine receptor channel required for normal muscle contraction/relaxation, and $Ca^{2+}$ is stored in the sarcoplasmic reticulum in an amount sufficient for the transmission of $Ca^{2+}$ signals from the sarcoplasmic reticulum.

Stabilization or maintenance of the aforementioned ryanodine receptor function can be attained by, for example, inhibiting reduction of the bonding strength between RyR and FKBP12.6, inhibiting phosphorylation of the ryanodine receptor, or maintaining the structure of the ryanodine receptor.

No particular limitation is imposed on the aforementioned homologue, so long as the homologue exhibits substantially the same $Ca^{2+}$ leakage inhibitory effect as the polypeptide having the amino acid sequence of any of SEQ ID NOs. 3 to 9. As used herein, the expression "substantially the same" refers to the case where the $Ca^{2+}$ leakage inhibitory effect of the homologue is physiochemically or pharmacologically the same as that of the polypeptide. The homologue and the polypeptide may differ from each other in terms of the extent of $Ca^{2+}$ leakage inhibitory effect, or quantitative factors (e.g., protein molecular weight).

Preferably, the invention polypeptide having a modified amino acid sequence described in (b) above is substantially the same as the polypeptide having the amino acid sequence of SEQ ID NO: 3 (i.e., non-modified amino acid sequence) in terms of, in addition to $Ca^{2+}$ leakage inhibitory effect, for example, the intrinsic activity of the non-modified polypeptide (e.g., the effect of stabilizing or maintaining ryanodine receptor activity in the case where the polypeptide is a ryanodine receptor stabilizer), antigenicity, or immunogenic activity.

In the present specification, the activities of the polypeptides (a) and (b); for example, $Ca^{2+}$ leakage inhibitory effect, effect of improving abnormal calcium handling (regulation), effect of stabilizing ryanodine receptor function, effect of maintaining (improving) ryanodine receptor function, effect of inhibiting reduction of the bonding strength between the ryanodine receptor and the FK506-binding protein, effect of inhibiting phosphorylation of the ryanodine receptor, and effect of maintaining the ryanodine receptor structure, may hereinafter be referred to simply as "$Ca^{2+}$ leakage inhibitory activity."

The $Ca^{2+}$ leakage inhibitory effect of the invention polypeptide corresponds to the case where, when a substance which induces $Ca^{2+}$ leakage is administered to a cell or tissue provided with the ability to express the invention polypeptide, in the cell or tissue, $Ca^{2+}$ leakage is inhibited, or $Ca^{2+}$ concentration in the endoplasmic reticulum is increased, as compared with the case of a cell or tissue which is not provided with such expression ability. More specifically, the $Ca^{2+}$ leakage inhibitory effect of the invention polypeptide corresponds to the effect of inhibiting $Ca^{2+}$ leakage in the endoplasmic reticulum of a cell or a tissue, the $Ca^{2+}$ leakage being induced by, for example, a substance (e.g., FK506) which cuts the bond between ryanodine receptor and FKBP12.6, thereby releasing $Ca^{2+}$ to cytoplasm, or a substance which cuts the bond between ryanodine receptor and FKBP12.6 through phosphorylation of the ryanodine receptor with protein kinase A (PKA).

As described above, the invention polypeptide has an amino acid sequence corresponding to a portion of the amino acid sequence of human ryanodine receptor type 2. Expression of the human ryanodine receptor has been found in various human tissues. The human ryanodine receptor has been found to have three subtypes; i.e., RyR1, which is localized in skeletal muscle and the brain (in particular, the cerebellum); RyR2, which is localized in myocardium, smooth muscle, and the brain (entire brain); and RyR3, which is present in the brain (in particular, the hippocampus and thalamus), smooth muscle, and skeletal muscle. Recent studies have reported dysfunction or reduced expression of RyR2 in a diabetic animal model [Bidasee, et al., Mol. Pharmacol., 60, 1356-1364 (2001); Okamoto, et al., Diabetologia, 40, 1485-1491 (1997)], which suggests involvement of RyR2 in diabetic conditions.

The invention polypeptide exhibits the effect of inhibiting $Ca^{2+}$ leakage in the endoplasmic reticulum of a cell or a tissue, and thus the polypeptide can be employed as an active ingredient of a drug. As described below, studies have reported the relation between $Ca^{2+}$ leakage and various diseases. According to these studies, a drug containing the invention polypeptide as an active ingredient may be employed for the treatment of such a disease.

Heart failure: Heart failure is a terminal event (syndrome) of various heart diseases. In heart failure, regardless of the original heart disease, an increase in calcium concentration in cytoplasm in diastole has been reported. Such calcium overload is closely related to calcium leakage via ryanodine receptor (Non-Patent Document 8), and thus use of a substance which inhibits such calcium leakage may provide a new promising strategy for the treatment of heart failure.

Cardiomyopathy: In hypertrophic cardiomyopathy, progression of hypertrophy has been shown to have a close relation to calcineurin, which is a calcium regulatory protein [Sussman M. A. et al., Science, 281: 1690-1693 (1998)]. Inhibition of intracellular calcium overload is considered effective for inhibiting progression of cardiac hypertrophy. Cardiomyopathy finally progresses, through reduction of myocardial contractile force, to heart failure. As described above, heart failure is closely related to calcium leakage (Non-Patent Document 8), and thus use of a substance which inhibits such calcium leakage may provide a new promising strategy for the treatment of cardiomyopathy.

Valvulopathy: Cardiac valvulopathy is a disease in which valvular insufficiency or valvular stenosis occurs, and load is chronically applied to the heart, finally leading to heart failure. Valvulopathy finally progresses, through reduction of myocardial contractile force, to heart failure. As described above, heart failure is closely related to calcium leakage (Non-Patent Document 8), and thus use of a substance which inhibits such calcium leakage may provide a new promising strategy for the treatment of valvulopathy.

Ischemic heart disease: As has been known, during ischemic reperfusion, many abnormalities occur in sarcoplasmic reticulum as well as in NCX, mitochondria, etc., which results in marked intracellular calcium overload. The extent of the role of ryanodine receptor in such calcium overload has not yet been elucidated, but JTV519, which has previously been shown by the present inventors to act on ryanodine receptor in the case of heart failure, is known to be effective for ischemic reperfusion injury [Hypertens. Res., 25: 303-9 (2002)]. Therefore, inhibition of calcium leakage is considered effective for reperfusion injury in ischemic heart disease, and a substance which inhibits calcium leakage may be employed as a new therapeutic agent for ischemic heart disease.

Myocardial infarction: Similar to the case of the aforementioned ischemic heart disease, inhibition of calcium leakage is considered effective for reperfusion injury in myocardial infarction. In addition, inhibition of calcium leakage is considered effective for prevention of heart failure in a post-myocardial infarction patient, and therefore a substance which inhibits calcium leakage may be employed as a new therapeutic agent for myocardial infarction.

Angina pectoris: Similar to the case of the aforementioned ischemic heart disease, inhibition of calcium leakage is considered effective for reperfusion injury in angina pectoris. Therefore, a substance which inhibits calcium leakage may be employed as a new therapeutic agent for angina pectoris.

Arrhythmia: Mutation of myocardial ryanodine receptor tends to cause calcium leakage (in the form of channel property), and fatal arrhythmia (in the form of disease) [Annu. Rev. Med., 54: 257-67 (2003)]. This fact implies that calcium leakage via ryanodine receptor is closely related to fatal arrhythmia. Therefore, use of a substance which inhibits such calcium leakage may provide a new strategy for the treatment of arrhythmia.

Hypertension and peripheral circulatory disorder: Onset of arteriosclerosis is related to an increase in intracellular $Ca^{2+}$ concentration in vascular smooth muscle. Intracellular $Ca^{2+}$ concentration in vascular smooth muscle is generally regulated by IP3 receptor. Recent studies have shown that ryanodine receptor is also distributed in vascular smooth muscle, and is involved in regulation of such $Ca^{2+}$ concentration [Circulation Research, 89: 1051-1067 (2001)]. Inhibition of calcium leakage via ryanodine receptor may also inhibit arteriosclerosis in vessel walls. Therefore, a substance which inhibits calcium leakage may be employed as an ameliorating agent for hypertension and peripheral circulatory disorder.

Diabetes: Insulin secretion in β cells is closely related to calcium release via ryanodine receptor mediated by FKBP12.6 [J. Biol. Chem., 272: 3133-6 (1997)]. A substance which inhibits calcium leakage via ryanodine receptor may be employed for normalization of insulin secretion, and treatment of diabetes.

Dysmnesia: Abnormality in ryanodine receptor has been reported in Alzheimer's disease [Neuroscience, 92: 499-513 (1999)]. Therefore, a substance which corrects such abnormality may be employed for the treatment of Alzheimer's disease or dysmnesia.

Cerebral infarction: Cell death during cerebral ischemia is closely related to an increase in intracellular $Ca^{2+}$ concentration. A large amount of ryanodine receptor is present in the endoplasmic reticulum of brain neuron, and dantrolene, which is a ryanodine receptor inhibitor, has been reported to inhibit neuron death during cerebral ischemia [Neurosci. Lett., 158: 105-108 (1993)]. Therefore, a substance which inhibits calcium leakage via ryanodine receptor may considerably reduce neuron death during cerebral ischemia, and the substance may be employed as a therapeutic agent for cerebral infarction.

Malignant hyperthermia: Malignant hyperthermia is a fatal genetic disease in which $Ca^{2+}$ is released from skeletal muscle ryanodine receptor during anesthesia, causing high fever and muscle contracture, the disease resulting from enhancement of the sensitivity of skeletal muscle ryanodine receptor to an anesthetic (e.g., halothane) through mutation of the ryanodine receptor. The channel regulatory domain of skeletal muscle ryanodine receptor is involved in such abnormal enhancement of the sensitivity to halothane. Therefore, a substance which regulates abnormal calcium handling may promote stabilization of ryanodine receptor, and may be employed as a new therapeutic drug for malignant hyperthermia.

As described above, there have been reported the relation between inhibition of $Ca^{2+}$ leakage in endoplasmic reticulum and onset of a disease such as heart failure, cardiomyopathy, valvulopathy, ischemic heart disease, myocardial infarction, angina pectoris, arrhythmia, hypertension, peripheral circulatory disorder, diabetes, dysmnesia, cerebral infarction, or malignant hyperthermia, and as well the effect of inhibiting $Ca^{2+}$ leakage in endoplasmic reticulum associated with such a disease. The fact that the invention polypeptide exhibits the effect of inhibiting $Ca^{2+}$ leakage in endoplasmic reticulum suggests that the polypeptide per se inhibits $Ca^{2+}$ leakage in the sarcoplasmic reticulum of a target cell, and thus the polypeptide is useful for treating or preventing any of the aforementioned diseases.

[2] Polynucleotide (DNA Molecule) of the Present Invention

The polynucleotide of the present invention is any of the following polynucleotides (c), (d), and (e):

(c) a polynucleotide encoding a polypeptide having the amino acid sequence of any of SEQ ID NOs: 3 to 9;

(d) a polynucleotide which can be hybridized with the polynucleotide described in (c) above under stringent conditions, and which can produce a corresponding expression product; and (e) a polynucleotide which has a DNA sequence 80% or more homologous to the polynucleotide described in (c) above, and which can produce a corresponding expression product. An expression product of the polynucleotide of the present invention exhibits $Ca^{2+}$ leakage inhibitory effect in a target cell.

Among the polynucleotides of the present invention (hereinafter may be referred to as the "invention DNA molecule(s)"), the aforementioned polynucleotide (c) may be a DNA molecule containing a polynucleotide having the DNA sequence of any of SEQ ID NOs: 20 to 26 or the complementary strand thereof.

The invention DNA molecules (polynucleotides) also include the polynucleotide (d); i.e., a polynucleotide which is hybridizable with the aforementioned polynucleotide (c) under stringent conditions, and can express a product exhibiting $Ca^{2+}$ leakage inhibitory effect in a target cell. As used herein, the expression "hybridizable under stringent conditions" may refer to the case where, even when hybridization is performed in 0.2×SSC containing 0.1% SDS at 50° C., followed by washing in 1×SSC containing 0.1% SDS at 60° C., no dissociation occurs.

The invention DNA molecules (polynucleotides) also include the polynucleotide (e); i.e., a polynucleotide which has a DNA sequence 80% or more (preferably 95% or more, more preferably about 98% or more) homologous to the aforementioned polynucleotide (c), and which can express a product exhibiting $Ca^{2+}$ leakage inhibitory effect in a target cell (in particular, $Ca^{2+}$ leakage inhibitory effect in the sarcoplasmic reticulum of a target cell).

An essential requirement for such a polynucleotide (hereinafter may be referred to as a "modified polynucleotide") is that the polynucleotide can expresses a product exhibiting $Ca^{2+}$ leakage inhibitory effect in a target cell (in particular, $Ca^{2+}$ leakage inhibitory effect in the sarcoplasmic reticulum of a target cell). In other words, the requirement is that a transformant obtained through transformation with a recombinant expression vector in which such a polynucleotide (modified polypeptide) has been inserted can express a protein exhibiting $Ca^{2+}$ leakage inhibitory effect in a target cell (in particular, $Ca^{2+}$ leakage inhibitory effect in the sarcoplasmic reticulum of a target cell).

The aforementioned modified polynucleotide encompasses a DNA molecule having a DNA sequence encoding an amino acid sequence (modified amino acid sequence) obtained through deletion, insertion, substitution, or addition of one or more amino acids in the amino acid sequence of any of SEQ ID NOs: 3 to 9 (in particular, SEQ ID NO: 3). Use of the modified polynucleotide may detect the non-modified invention DNA molecule.

The invention DNA molecule also encompasses homologues of a polynucleotide (RyR2 gene fragment) having the DNA sequence of any of SEQ ID NOs: 20 to 26. As used herein, the term "homologues of RyR2 gene fragment" refers to a series of related DNA molecules which have sequence homology to the DNA sequence of any of SEQ ID NOs: 20 to 26, and which are recognized as one DNA molecule family in terms of commonality in structural feature and polynucleotide expression pattern, and as well similarity in biological function. The homologues also include alleles of the RyR2 gene fragment.

Modification (variation) or the like of an amino acid sequence may naturally occur through, for example, mutation or post-translational modification. Such amino acid sequence modification may be artificially performed by use of a naturally occurring DNA molecule (e.g., the RyR2 gene fragment according to the present invention). The invention DNA molecule encompasses all the modified DNA molecules having the aforementioned properties, regardless of, for example, the cause and means of such modification or variation.

Examples of the aforementioned artificial means include genetic engineering techniques such as site-specific mutagenesis [Methods in Enzymology, 154, 350, 367-382 (1987); Methods in Enzymology, 100, 468 (1983); Nucleic Acids Res., 12, 9441 (1984); and *Zoku Seikagaku Jikken Koza* 1 *"Idenshi Kenkyuho* II," edited by The Japanese Biochemical Society, p. 105 (1986)]; chemical synthesis means such as the phosphotriester method and the phosphoramidite method [J. Am. Chem. Soc., 89, 4801 (1967); J. Am. Chem. Soc., 91, 3350 (1969); Science, 150, 178 (1968); Tetrahedron Lett., 22, 1859 (1981); and Tetrahedron Lett., 24, 245 (1983)]; and combinations of these techniques and means. More specifically, DNA synthesis may be performed through chemical synthesis employing the phosphoramidite method or the phosphotriester method, or may be performed by means of a commercially available automated oligonucleotide synthesizer. A double-stranded fragment can be obtained by annealing a synthesized complementary strand with a chemically synthesized single strand under appropriate conditions, or adding a synthesized complementary strand to a chemically synthesized single strand by use of an appropriate primer sequence and DNA polymerase.

The nucleotide sequence of a DNA molecule having the DNA sequence of any of SEQ ID NOs: 20 to 26, which molecule is one specific embodiment of the invention DNA molecule (e.g., human RyR2 gene fragment), is an example of a combination of codons encoding the amino acid residues of a polypeptide having the corresponding amino acid sequence represented by any of SEQ ID NOs: 3 to 9. The invention DNA molecule is not limited to a DNA molecule having such a specific DNA sequence, and may have a DNA sequence obtained through arbitrary combination and choice of codons for the amino acid residues of the invention polypeptide. Choice of codons can be performed through a customary method. Codon choice may be performed in consideration of, for example, the codon usage of a host to be employed [Nucleic Acids Res., 9, 43 (1981)].

[3] Production of the Invention DNA Molecule

The invention DNA molecule can be easily produced or obtained through a chemical DNA synthesis method for directly synthesizing a DNA molecule having a nucleic acid sequence encoding a portion of the RyR2 amino acid sequence, on the basis of the sequence data of a specific example of the nucleic acid sequence of the RyR2 gene fragment (i.e., the invention polypeptide) disclosed herein, or on the basis of the sequence data of a portion of the RyR2 amino acid sequence. Alternatively, the invention DNA molecule can be easily produced or obtained through a generally employed genetic engineering technique [see, for example, Molecular Cloning 2nd Ed, Cold Spring Harbor Lab. Press (1989); and *Zoku Seikagaku Jikken Koza "Idenshi Kenkyuho* I, II, III," edited by The Japanese Biochemical Society (1986)].

In such a chemical DNA synthesis method for directly synthesizing a DNA molecule, for example, a DNA molecule can be easily synthesized through solid-phase synthesis employing the phosphoramidite method by means of an automated synthesizer.

Production of the invention DNA molecule through a genetic engineering technique can be specifically performed by preparing, through a customary method, a cDNA library from an appropriate source in which the DNA molecule is expressed, and selecting a desired clone from the library by use of an appropriate probe or antibody specific to the invention DNA molecule [e.g., Proc. Natl. Acad. Sci., USA., 78, 6613 (1981); and Science, 222, 778 (1983)].

Examples of the aforementioned cDNA source include various cells and tissues expressing the gene of the present invention, and cultured cells derived therefrom. Isolation of total RNA from such a source, isolation and purification of mRNA, obtainment of cDNA, cloning thereof, etc. can be performed through a customary method. Production of the gene of the present invention can also be performed by means of various commercially available mRNA or cDNA libraries (e.g., mRNA or cDNA libraries available from Clontech Lab. Inc.), in particular, human heart mRNA or cDNA libraries.

No particular limitation is imposed on the method for screening the invention DNA molecule from cDNA libraries, and such screening can be performed through a customary method. Specific examples of the screening method include a method in which a protein produced by cDNA is subjected to immunological screening by use of an antibody specific to the protein, thereby selecting the corresponding cDNA clone; plaque hybridization and colony hybridization employing a probe which is selectively bound to a target DNA sequence; and combinations of these methods.

The probe employed in the aforementioned method is generally DNA which is chemically synthesized on the basis of data of the DNA sequence of the invention DNA molecule. The gene of the present invention which has already been obtained or a fragment of the gene can be advantageously employed as the aforementioned probe. Furthermore, a sense primer or antisense primer designed on the basis of the DNA sequence data of the invention DNA molecule can be employed as a screening probe.

The polynucleotide employed as a probe is a partial polynucleotide corresponding to SEQ ID NO: 20, and has at least 15 continuous nucleotides, preferably at least 20 continuous nucleotides, more preferably at least 30 continuous nucleotides. The aforementioned positive clone per se for producing the invention DNA molecule can also be employed as a probe.

DNA/RNA amplification through PCR [Science, 230, 1350 (1985)] is preferably employed for obtaining the gene of the present invention. Particularly when full-length cDNA is difficult to obtain from a library, RACE [Rapid amplification of cDNA ends; *Jikken Igaku*, 12(6), 35 (1994)], in particular, 5'-RACE [M. A. Frohman, et al., Proc. Natl. Acad. Sci., USA., 8, 8998 (1988)], etc. is preferably employed.

The primer employed for performing PCR can be designed on the basis of the sequence data of the gene of the present invention as disclosed herein, and can be synthesized through a customary method. Isolation and purification of DNA/RNA fragments amplified by PCR can be performed through a customary method (e.g., gel electrophoresis).

The above-obtained invention DNA molecule or DNA fragments can be sequenced through a customary method; for example, the dideoxy method [Proc. Natl. Acad. Sci., U.S.A., 74, 5463 (1977)] or the Maxam-Gilbert method [Methods in Enzymology, 65, 499 (1980)], or can be conveniently sequenced by means of a commercially available sequencing kit.

[4] Genetic Engineering Production of the Invention Polypeptide

The invention polypeptide (expression product) can be easily and reliably mass-produced by use of the gene of the present invention through a generally employed genetic engineering technique (e.g., Science, 224, 1431 (1984); Biochem. Biophys. Res. Comm., 130, 692 (1985); or Proc. Natl. Acad. Sci., USA., 80, 5990 (1983)) in the form of an expression product of the gene or a protein containing the expression product. More specifically, the invention polypeptide (expression product) can be obtained through the following procedure: recombinant DNA (expression vector) which enables a gene encoding a desired protein to be expressed in a host cell is prepared; the thus-prepared vector is introduced into the host cell for transformation; the resultant transformant is cultured; and a target protein is collected from the resultant culture.

The present invention also provides, for example, a polypeptide encoded by the invention DNA molecule (polynucleotide); a vector containing, for example, the invention DNA molecule, and a host cell transformed with the vector, the vector and host cell being employed for producing the polypeptide; and a method for producing the invention polypeptide through culturing of the host cell.

The aforementioned host cell may be derived from prokaryote or eukaryote. For example, the prokaryotic host may be any of generally employed hosts such as *Escherichia coli* and *Bacillus subtilis*. Preferably, *Escherichia coli*, in particular, *Escherichia coli* K12 strain is employed. Examples of eukaryotic host cells include vertebrate cells and yeast cells. Preferred vertebrate cells to be employed include COS cell (i.e., simian cell) [Cell, 23: 175 (1981)], Chinese hamster ovary cell, and dihydrofolate reductase-deficient Chinese hamster ovary cell line [Proc. Natl. Acad. Sci., USA., 77: 4216 (1980)]; and preferred yeast cells to be employed include *Saccharomyces* yeast cell. Needless to say, the host cell to be employed is not limited to these examples.

In the case where the host is a prokaryotic cell, a vector which can be replicated in the host cell is employed. In such a case, preferably, there is employed an expression plasmid in which a promoter sequence, a Shine-Dalgarno (SD) sequence, and an initiation codon (e.g., ATG) required for protein synthesis initiation are provided upstream of the gene of the present invention so that the gene can be expressed in the vector. In general, an *Escherichia coli*-derived plasmid (e.g., pBR322, pBR325, pUC12, or pUC13) is often employed as the aforementioned vector. However, the vector to be employed is not limited to these examples, and may be any known vector. Examples of commercially available vectors to be used in an expression system employing *Escherichia coli* include pGEX-4T (Amersham Pharmacia Biotech), pMAL-C2 and pMAL-P2 (New England Biolabs), pET21 and pET21/lacq (Invitrogen), and pBAD/His (Invitrogen).

In the case where the host is a vertebrate cell, an expression vector to be employed generally contains a promoter, a RNA splice site, a polyadenylation site, and a transcription termination sequence, which are located upstream of the gene of the present invention to be expressed. If necessary, the expression vector may further contain a replication origin. Specific examples of the expression vector include pSV2dhfr having an SV40 initial promoter [Mol. Cell. Biol., 1: 854 (1981)]. The expression vector may be any known commercially available vector other than the aforementioned ones. Examples of commercially available vectors to be used in an expression system employing an animal cell include vectors for animal cells, such as pEGFP-N and pEGFP-C (Clontech), pIND (Invitrogen), and pcDNA3.1/His (Invitrogen); and vectors for insect cells, such as pFastBac HT (GibcoBRL), pAcGHLT (PharMingen), and pAc5/V5-His, pMT/V5-His, and pMT/Bip/V5-his (Invitrogen).

Specific examples of expression vectors to be employed in the case where the host is a yeast cell include pAM82 having a promoter for acid phosphatase gene [Proc. Natl. Acad. Sci., USA., 80: 1 (1983)]. Commercially available expression vectors for yeast cell include pPICZ (Invitrogen) and pPICZα (Invitrogen).

No particular limitation is imposed on the promoter to be employed. In the case where the host is a bacterium belonging to the genus *Escherichia*, for example, tryptophan (trp) promoter, lpp promoter, lac promoter, recA promoter, or PL/PR promoter is preferably employed. In the case where the host is a bacterium belonging to the genus *Bacillus*, SP01 promoter, SP02 promoter, penP promoter, or the like is preferably employed. In the case where the host is yeast, for example, pH05 promoter, PGK promoter, GAP promoter, or ADH promoter is preferably employed. In the case where the host is an animal cell, for example, SV40-derived promoter, retrovirus promoter, metallothionein promoter, heat shock promoter, cytomegalovirus promoter, or SRα promoter is preferably employed.

A typical fusion protein expression vector is also preferably employed as the expression vector for the invention DNA molecule. Specific examples of the vector include pGEX (Promega) for expressing the DNA molecule in the form of a fusion protein with glutathione-S-transferase (GST).

When the sequence encoding a mature polypeptide corresponds to the sequence of a polynucleotide which promotes expression or secretion of the polypeptide from a host cell, the polynucleotide sequence is, for example, a secretion sequence or a leader sequence. When the host is a bacterium, such a sequence contains a marker sequence (hexahistidine tag or histidine tag) employed for purification of a fusion mature polypeptide, whereas when the host is a mammalian cell, such a sequence contains a hemagglutinin (HA) tag.

No particular limitation is imposed on the method for introducing a desired recombinant DNA (expression vector) into a host cell and on the transformation method employing the expression vector, and generally employed introduction and transformation methods can be employed.

The thus-transformed cell can be cultured through a customary method, and, through this culturing, a target protein encoded by a gene designed as desired is expressed and produced (accumulated or secreted) inside or outside the transformed cell, or on the membrane of the cell.

The medium employable for such culturing can be appropriately selected from among conventionally employed media in consideration of the type of a host cell to be employed, and the culturing can be performed under conditions suitable for growth of the host cell.

If desired, the thus-obtained recombinant protein (the invention polypeptide) can be subjected to isolation and purification through various separation methods utilizing, for example, physical and chemical properties of the protein [see, for example, "Biochemical Data Book II," pp. 1175-1259, 1st Edition, 1st Impression, Jun. 23, 1980, published by Tokyo Kagaku Dojin Co., Ltd.; Biochemistry, 25 (25), 8274 (1986); and Eur. J. Biochem., 163, 313 (1987)].

Specific examples of such separation methods include common reconstitution treatment, treatment with a protein precipitant (salting out), centrifugation, the osmotic shock method, ultrasonic disruption, ultrafiltration, molecular sieve chromatography (gel filtration), adsorption chromatography, ion-exchange chromatography, affinity chromatography, various liquid chromatography techniques such as high performance liquid chromatography (HPLC), dialysis, and combinations of these methods. Particularly preferred methods include affinity chromatography employing a column to which an antibody specific to the invention polypeptide is bound.

The polynucleotide encoding the invention polypeptide can be designed by use of the RyR2 gene DNA sequence of SEQ ID NO: 2. If desired, in the gene, codons corresponding to amino acid residues may be appropriately selected and changed.

In the amino acid sequence encoded by the RyR2 gene, when a portion of the amino acid residues (or amino acids) of the sequence is to be modified through substitution, insertion, deletion, addition, etc., any of the aforementioned methods (e.g., site-specific mutagenesis) can be employed.

[5] Expression Product of the Present Invention

An expression product of the invention polynucleotide, the expression product serving as an active ingredient of the pharmaceutical composition of the present invention and being employed in the screening method of the present invention (hereinafter the expression product may be referred to as the "invention expression product"), can be obtained through a genetic engineering technique described in [4] above.

Similar to the case of the invention polypeptide described in [1] above, the invention expression product exhibits $Ca^{2+}$ leakage inhibitory effect in a target cell (in particular, $Ca^{2+}$ leakage inhibitory effect in sarcoplasmic reticulum), and is useful as the aforementioned therapeutic or preventive agent.

[6] Chemical Synthesis of the Invention Polypeptide

The invention polypeptide can also be produced through a generally employed chemical synthesis method on the basis of data of the amino acid sequences of SEQ ID NOs: 3 to 9. The chemical synthesis method encompasses peptide synthesis through a generally employed liquid-phase method or solid-phase method.

More specifically, the peptide synthesis encompasses so-called stepwise elongation, in which amino acids are connected step-by-step in turn on the basis of amino acid sequence data, thereby elongating an amino acid chain; and fragment condensation, in which fragments, each containing several amino acids, are synthesized in advance, and then the fragments are subjected to coupling reaction. The invention polypeptide can be synthesized through any of these techniques.

Condensation employed in such peptide synthesis can be performed through a customary method. For example, such condensation can be performed through the azide method, the mixed-acid anhydride method, the DCC method, the active ester method, the redox method, the DPPA (diphenylphosphoryl azide) method, the DCC+additive (e.g., 1-hydroxybenzotriazole, N-hydroxysuccinamide, or N-hydroxy-5-norbornene-2,3-dicarboxyimide) method, or the Woodward method.

The solvent to be used in these methods can be appropriately selected from among solvents which are generally known to be employed in such peptide condensation. Examples of such a solvent include dimethylformamide (DMF), dimethyl sulfoxide (DMSO), hexaphosphoramide, dioxane, tetrahydrofuran (THF), ethyl acetate, and mixtures thereof.

Upon the aforementioned peptide synthesis, the carboxyl groups of amino acids or peptides which do not participate in reaction can be generally protected through esterification, for example, in the form of a lower alkyl ester (e.g., methyl ester, ethyl ester, or tert-butyl ester), or an aralkyl ester (e.g., benzyl ester, p-methoxybenzyl ester, or p-nitrobenzyl ester).

A functional group of the side chain of an amino acid (e.g., the hydroxyl group of a tyrosine residue) may be protected with, for example, an acetyl group, a benzyl group, a benzyloxycarbonyl group, or a tert-butyl group, but such protection is not necessarily performed. For example, the guanidino group of an arginine residue may be protected with an appropriate protective group such as a nitro group, a tosyl group, a p-methoxybenzenesulfonyl group, a methylene-2-sulfonyl group, a benzyloxycarbonyl group, an isobornyloxycarbonyl group, or an adamantyloxycarbonyl group.

Reaction for removing such a protective group from the thus-protected amino acid, peptide, or finally produced invention polypeptide can also be performed through a conventionally employed method; for example, catalytic reduction, or a method employing liquid ammonia/sodium, hydrogen fluoride, hydrogen bromide, hydrogen chloride, trifluoroacetic acid, acetic acid, formic acid, methanesulfonic acid, or the like.

The thus-obtained invention polypeptide can be appropriately purified through any of the aforementioned methods; for example, a method which is generally employed in the field of peptide chemistry, such as ion-exchange resin chromatography, partition chromatography, gel chromatography, or countercurrent distribution.

[7] Pharmaceutical Composition of the Present Invention

The pharmaceutical composition of the present invention contains, as an active ingredient, the invention polypeptide or the invention expression product. The pharmaceutical composition is useful as, for example, a pharmaceutical composition exhibiting $Ca^{2+}$ leakage inhibitory effect in a target cell (in particular, $Ca^{2+}$ leakage inhibitory effect in sarcoplasmic reticulum), or an agent for improving calcium handling (regulation). The pharmaceutical composition, which exhibits the aforementioned $Ca^{2+}$ leakage inhibitory effect and calcium handling (regulation) improving effect, is also useful as a therapeutic or preventive agent for, for example, heart failure, cardiomyopathy, valvulopathy, ischemic heart disease, myocardial infarction, angina pectoris, arrhythmia, hypertension, peripheral circulatory disorder, diabetes, dysmnesia, cerebral infarction, or malignant hyperthermia.

More specifically, the invention polypeptide or the invention expression product (e.g., R2P), which serves as an active ingredient of the pharmaceutical composition of the present invention, exhibits the effect of inhibiting $Ca^{2+}$ leakage induced by FK506 or the like in a sarcoplasmic reticulum specific thereto. This $Ca^{2+}$ leakage inhibitory effect (or activity) can be employed for the treatment of diseases associated with $Ca^{2+}$ leakage induction or with abnormal calcium handling in cells. Examples of target cells affected by such $Ca^{2+}$ leakage induction or abnormal calcium handling include myocardial cell, smooth muscle cell, skeletal muscle cell, brain neuron, neuroblast, and pancreatic β cell. Examples of important tissues containing such cells include heart, arterial vessel, muscle tissue, cerebellum, cerebral cortex, midbrain, cranial nerve tissue (e.g., hypophysis), and pancreas.

Examples of the aforementioned sarcoplasmic reticulum include sarcoplasmic reticulum prepared from normal or failing myocardium, sarcoplasmic reticulum prepared from vascular smooth muscle, and sarcoplasmic reticulum prepared from skeletal muscle.

The invention polypeptide or the invention expression product, which is an active ingredient of the pharmaceutical composition of the present invention, also encompasses pharmaceutically acceptable salts thereof. Examples of such salts include nontoxic alkali metal salts, alkaline earth metal salts, and ammonium salts which are prepared through methods well known in the art, such as sodium, potassium, lithium, calcium, magnesium, barium, and ammonium salts. The aforementioned salts also encompass nontoxic acid addition salts prepared through reaction between the invention polypeptide or the invention expression product and an appropriate organic acid or inorganic acid. Typical examples of nontoxic acid addition salts include hydrochloride, hydrobromide, sulfate, bisulfate, acetate, oxalate, valerate, oleate, laurate, borate, benzoate, lactate, phosphate, p-toluenesulfonate (tosylate), citrate, maleate, fumarate, succinate, tartrate, sulfonate, glycolate, ascorbate, benzenesulfonate, and napsylate.

The pharmaceutical composition of the present invention, which contains, as an active ingredient, the invention polypeptide, the invention expression product, or a salt thereof, is prepared into the form of a pharmaceutical product containing a pharmaceutically effective amount of the active ingredient and an appropriate pharmaceutical carrier or diluent.

Examples of the pharmaceutical carrier employed for preparation of such a pharmaceutical product include diluents and excipients, such as a filler, an extender, a binder, a humectant, a disintegrant, a surfactant, and a lubricant, which are generally employed in accordance with the pharmaceutical product form. Such a carrier is appropriately selected so as to fit the unit dosage form of the prepared pharmaceutical product. A particularly preferred pharmaceutical product is prepared by use of an appropriate ingredient which is commonly employed for protein preparations, etc., such as a stabilizer, a bactericide, a buffer, an isotonizing agent, a chelating agent, a pH-adjusting agent, or a surfactant.

Examples of the aforementioned stabilizer include human serum albumin, common L-amino acids, sugars, and cellulose derivatives. Such a stabilizer may be employed singly or in combination with, for example, a surfactant. Particularly, this combination may further enhance the stability of the active ingredient. No particular limitation is imposed on the L-amino acid to be employed, and the L-amino acid may be any of glycine, cysteine, glutamic acid, and the like. No particular limitation is imposed on the sugar to be employed, and examples of the sugar which may be employed include monosaccharides such as glucose, mannose, galactose, and fructose; sugar alcohols such as mannitol, inositol, and xylitol; disaccharides such as sucrose, maltose, and lactose; polysaccharides such as dextran, hydroxypropyl starch, chondroitin sulfate, and hyaluronic acid; and derivatives thereof. No particular limitation is imposed on the surfactant to be employed, and the surfactant may be any of an ionic surfactant or a nonionic surfactant. Specific examples of the surfactant which may be employed include polyoxyethylene glycol sorbitan alkyl esters, polyoxyethylene alkyl ethers, sorbitan monoacyl esters, and fatty acid glycerides. No particular limitation is imposed on the cellulose derivative to be employed, and the cellulose derivative may be, for example, methylcellulose, ethylcellulose, hydroxyethylcellulose, hydroxypropylcellulose, hydroxypropylmethylcellulose, or carboxymethylcellulose sodium.

The appropriate amount of a sugar to be added is about 0.0001 mg or more, preferably within a range of about 0.01 to about 10 mg, on the basis of 1 μg of the active ingredient. The appropriate amount of a surfactant to be added is about 0.00001 mg or more, preferably within a range of about 0.0001 to about 0.01 mg, on the basis of 1 μg of the active ingredient. The appropriate amount of human serum albumin to be added is about 0.0001 mg or more, preferably within a range of about 0.001 to about 0.1 mg, on the basis of 1 μg of the active ingredient. The appropriate amount of an L-amino acid to be added is about 0.001 to about 10 mg on the basis of 1 μg of the active ingredient. The appropriate amount of a cellulose derivative to be added is about 0.00001 mg or more, preferably within a range of about 0.001 to about 0.1 mg, on the basis of 1 μg of the active ingredient.

The amount of the active ingredient contained in the pharmaceutical composition of the present invention is appropriately determined within a wide range. The appropriate active ingredient content of the composition is generally about 0.00001 to about 70 wt. %, preferably about 0.0001 to about 5 wt. %.

The pharmaceutical composition of the present invention may also contain an additive such as a buffer, an isotonizing agent, or a chelating agent. Examples of the buffer include boric acid, phosphoric acid, acetic acid, citric acid, ε-aminocaproic acid, glutamic acid, and/or salts corresponding to these acids (e.g. alkali metal salts and alkaline earth metal salts of these acids, such as sodium, potassium, calcium, and magnesium salts). Examples of the isotonizing agent include sodium chloride, potassium chloride, sugars, and glycerin. Examples of the chelating agent include sodium edetate and citric acid.

The pharmaceutical composition of the present invention may be prepared in the form of a solution product. Alternatively, the composition may take the form of a storable lyophilized product which is prepared through lyophilization of the solution product so that the lyophilized product is dissolved in, for example, a buffer (including water or saline) upon use to prepare a solution of appropriate concentration.

The unit dosage form of the pharmaceutical composition of the present invention can be appropriately selected so as to meet the therapeutic purpose. Typical examples of the dosage form include solid forms such as a tablet, a pill, a dispersion, a powder, a granule, and a capsule; and liquid forms such as a solution, a suspension, an emulsion, a syrup, and an elixir. In accordance with administration routes, these dosage forms are further classified into, for example, an oral agent, a parenteral agent, a nasal agent, a vaginal agent, a suppository, a sublingual agent, and an ointment, which can be respectively formulated, molded, or prepared through a customary method. If necessary, the pharmaceutical composition of the present invention may contain, for example, a coloring agent, a preservative, a perfume, a flavoring agent, a sweetening agent, or another drug.

No particular limitation is imposed on the method for administration of the pharmaceutical composition of the present invention, and the administration method is determined on the basis of, for example, the product form, age, sex, and other conditions of the patient, and the severity of disease. For example, a tablet, a pill, a solution, a suspension, an emulsion, a granule, or a capsule is orally administered; an injection is intravenously administered singly or in combination with a common replacement fluid (e.g., glucose or amino acid), and is, if necessary, intramuscularly, intradermally, subcutaneously, or intraperitoneally administered singly; a suppository is intrarectally administered; a vaginal agent is intravaginally administered; a nasal agent is intranasally administered; a sublingual agent is intraorally administered; and an ointment is locally administered through a transdermal route.

No particular limitation is imposed on the dose of the active ingredient contained in the pharmaceutical composition of the present invention, and the dose is appropriately determined within a wide range in consideration of, for example, the desired therapeutic effect, the administration method, the treatment period, and the age, sex, and other conditions of a patient. The daily dose is generally about 0.01 μg to about 10 mg per kg body weight, preferably about 0.1 μg to about 1 mg per kg body weight. The composition may be administered once daily or in several divided doses per day.

[8] Screening of Substance (Agonist) which Promotes $Ca^{2+}$ Leakage Inhibitory Effect and Substance (Antagonist) which Suppresses the Inhibitory Effect The present invention also provides a screening method for selecting a candidate compound which promotes or suppresses the $Ca^{2+}$ leakage inhibitory effect (or the effect of improving abnormal calcium handling (hereinafter may be referred to as the "abnormal calcium handling improving effect")) in the endoplasmic reticulum of a target cell.

A characteristic feature of the screening method resides in that, in the presence or absence of a test substance, the level of the $Ca^{2+}$ leakage inhibitory effect (or the abnormal calcium handling improving effect) of the invention polypeptide or an expression product of the invention polypeptide in the endoplasmic reticulum of a target cell is measured; and the level measured in the presence of the test substance is compared with the level measured in the absence of the test substance, to thereby select the test substance as an agonist which enhances the inhibitory effect or as an antagonist which suppresses the inhibitory effect.

The level of the $Ca^{2+}$ leakage inhibitory effect or the abnormal calcium handling improving effect of the invention polypeptide in a target cell (particularly in the endoplasmic reticulum) is determined through, for example, the following procedure: firstly, in the presence or absence of the invention polypeptide and in the presence or absence of a test substance, the amount of $Ca^{2+}$ taken into myocardium-derived endoplasmic reticulum is measured; subsequently, FK506 is added to the endoplasmic reticulum, to thereby cut the bond between ryanodine receptor and FKBP12.6 and to induce $Ca^{2+}$ leakage; and then the inhibitory effect of the polypeptide on FK506-induced $Ca^{2+}$ leakage in the endoplasmic reticulum of a cell or a tissue is determined on the basis of reduction of the amount of $Ca^{2+}$ leaked from the sarcoplasmic reticulum as detected by means of a $Ca^{2+}$ indicator.

The $Ca^{2+}$ leakage inhibitory effect in a target cell (in particular, the $Ca^{2+}$ leakage inhibitory effect in sarcoplasmic reticulum) or the abnormal calcium handling improving effect of the invention polypeptide or the invention expression product can be detected through a known method.

More specifically, $Ca^{2+}$ leakage induction or $Ca^{2+}$ leakage inhibitory effect can be detected, for example, as follow. (1) $Ca^{2+}$ leakage from sarcoplasmic reticulum and the effect of inhibiting the $Ca^{2+}$ leakage can be measured through, for example, the method described in M. Yano, et al., Circulation, 102, 2131-2136 (2000).

Specifically, for example, in the presence or absence of the invention polypeptide or the invention expression product, the amount of $Ca^{2+}$ taken into myocardium-derived sarcoplasmic reticulum is measured, and subsequently, FK506 is added to the sarcoplasmic reticulum, to thereby cut the bond between ryanodine receptor and FKBP12.6 and to induce $Ca^{2+}$ leakage. Thereafter, the inhibitory effect on FK506-induced $Ca^{2+}$ leakage in the endoplasmic reticulum of a cell or a tissue can be detected by means of a $Ca^{2+}$ indicator.

More specifically, sarcoplasmic reticulum is incubated with a calcium-containing buffer (free calcium concentration: 0.3 μmol/L), and ATP (0.5 mmol/L) is added to the resultant mixture, to thereby initiate $Ca^{2+}$ uptake into the cell. The time course of $Ca^{2+}$ uptake is measured by means of fluo 3 serving as a $Ca^{2+}$ indicator, and absorbance at an excitation wavelength of 480 nm and an emission wavelength of 530 nm is measured by means of an absorbance meter. After $Ca^{2+}$ uptake reaches a plateau, in the presence or absence of the invention polypeptide or the invention expression product, FK506 is added, and then $Ca^{2+}$ leakage is measured by means of the $Ca^{2+}$ indicator, whereby the $Ca^{2+}$ leakage inhibitory effect can be detected. In the aforementioned method, instead of FK506, rapamycin may be employed as a $Ca^{2+}$ leakage-inducing agent.

As used herein, "$Ca^{2+}$ leakage inhibitory activity" encompasses the $Ca^{2+}$ leakage inhibitory effect in endoplasmic reticulum, and as well the activity of the polypeptide exhibiting the abnormal calcium handling (regulation) improving effect, the effect of stabilizing ryanodine receptor function, the effect of maintaining (improving) ryanodine receptor function, the effect of inhibiting reduction of the bonding strength between ryanodine receptor and FK506-binding protein, the effect of inhibiting phosphorylation of ryanodine receptor, and/or the effect of maintaining the structure of ryanodine receptor. Therefore, furthermore, the below-exemplified detection method can be performed.

(2) For detection of the effect of inhibiting phosphorylation of ryanodine receptor, there can be detected the inhibitory effect on $Ca^{2+}$ leakage in the endoplasmic reticulum of a cell or a tissue, the $Ca^{2+}$ leakage being induced by a substance which cuts the bond between ryanodine receptor and FKBP12.6, and induces $Ca^{2+}$ leakage through phosphorylation of the ryanodine receptor with protein kinase A (PKA).

Specifically, the aforementioned ryanodine receptor phosphorylation inhibitory effect of the invention polypeptide or the invention expression product can be detected by, for example, measuring the extent of phosphorylation mediated by protein kinase A in the presence or absence of the invention polypeptide or the invention expression product [see, for example, Steven O, Marx, et al., Cell, 101, 365-376 (2000), or Reiken, et al., J. Biol. Chem., 278, 444-453 (2003)].

(3) The ryanodine receptor structure maintaining effect of the invention polypeptide or the invention expression product can be detected by, for example, observing a change in MCA fluorescence intensity in endoplasmic reticulum through the method described in Yano. M., et al., Circulation, 102, 2131-2136 (2000).

(4) The effect of inhibiting reduction of the bonding strength between ryanodine receptor and FK506-binding protein (specifically, the effect of inhibiting reduction of the bonding strength between ryanodine receptor (RyR) and FK506-binding protein 12.6 (FKBP12.6) of the invention polypeptide or the invention expression product) can be detected by, for example, measuring the bonding strength between RyR and FKBP12.6 through surface plasmon analysis or a similar technique.

Specifically, inhibition of reduction of the bonding strength between RyR and FKBP12.6 can be measured through, for example, the following procedure: to a chip on which RyR or FKBP12.6 has been immobilized, correspondingly, an FKBP12.6- or RyR-containing solution which contains the invention polypeptide or the invention expression product, or contains neither the invention polypeptide nor the invention expression product is fed at a constant flow rate; a sensorgram representing formation of an RyR-FKBP12.6 complex is obtained on the basis of a change in surface plasmon resonance signal; and inhibition of reduction of the bonding strength is measured through comparison between binding rates obtained from sensorgrams corresponding to the respective conditions.

(5) For detection of the abnormal calcium handling (regulation) improving effect, a change in $Ca^{2+}$ concentration in sarcoplasmic reticulum or the corresponding cell change, which is attributed to abnormal migration of $Ca^{2+}$ into or from the sarcoplasmic reticulum via stabilization of ryanodine receptor, can be detected through at least one of the aforementioned detection methods (1) to (4), to thereby detect whether or not the abnormal calcium handling will be corrected.

The present invention also provides a screening method for selecting a candidate substance which enhances the $Ca^{2+}$ leakage inhibitory effect (or the abnormal calcium handling improving effect) of the invention polypeptide in the endoplasmic reticulum of a target cell, which method comprises the following steps (1) to (5):

(1) a step of providing a target cell transformed with an expression vector containing a polynucleotide encoding the invention polypeptide;

(2) a step of adding FK506 to the endoplasmic reticulum of the target cell so as to induce $Ca^{2+}$ leakage in the presence or absence of a test substance;

(3) a step of measuring, by means of a $Ca^{2+}$ indicator, the amount of $Ca^{2+}$ leaked from the endoplasmic reticulum of the target cell, to thereby determine the amount of change in $Ca^{2+}$ leakage from the endoplasmic reticulum in the presence or absence of the test substance;

(4) a step of adding FK506 to the endoplasmic reticulum of a non-transformed cell so as to induce $Ca^{2+}$ leakage in the absence of the test substance, measuring by means of a $Ca^{2+}$ indicator the amount of $Ca^{2+}$ having leaked from the endoplasmic reticulum, and determining the difference between the amount of $Ca^{2+}$ as measured outside the endoplasmic reticulum; i.e., the standard amount, and each of the amounts as determined in (3) above in the presence and absence of the test substance; and (5) a step of selecting the test substance as a candidate substance when the difference between the standard amount and the amount as determined in the presence of the test substance is smaller than the difference between the standard amount and the amount as determined in the absence of the test substance.

The present invention also provides a screening method for selecting a candidate substance which enhances the $Ca^{2+}$ leakage inhibitory effect (or the abnormal calcium handling improving effect) of the invention expression product in the endoplasmic reticulum of a target cell, which method comprises the following steps (1) to (5):

(1) a step of providing a target cell transformed with an expression vector containing the invention polynucleotide;

(2) a step of adding FK506 to the endoplasmic reticulum of the target cell so as to induce $Ca^{2+}$ leakage in the presence or absence of a test substance;

(3) a step of measuring, through RT-PCR, the amount of expression of the polynucleotide in the endoplasmic reticulum of the target cell in the presence or absence of the test substance;

(4) a step of comparing the expression amount in the presence of the test substance with the expression amount in the absence of the test substance; and (5) a step of selecting the test substance as a candidate substance when the expression amount in the presence of the test substance is greater than the expression amount in the absence of the test substance.

The present invention also provides a screening method for selecting a candidate substance which enhances the $Ca^{2+}$ leakage inhibitory effect (or the abnormal calcium handling improving effect) of the invention polypeptide in a target cell, which method comprises the following steps (1) to (5):

(1) a step of providing a target cell transformed with an expression vector containing a polynucleotide encoding the invention polypeptide;

(2) a step of adding FK506 to the endoplasmic reticulum of the target cell so as to induce $Ca^{2+}$ leakage in the presence or absence of a test substance;

(3) a step of measuring, by means of an antibody against the polypeptide, the amount of the polypeptide produced in the target cell in the presence or absence of the test substance;

(4) a step of comparing the production amount in the presence of the test substance with the production amount in the absence of the test substance; and (5) a step of selecting the test substance as a candidate substance when the production amount in the presence of the test substance is greater than the production amount in the absence of the test substance.

In each of these screening methods, the amount of expression (or production) of the invention polypeptide represented by any of SEQ ID NOs: 3 to 9 (e.g., R2P represented by SEQ ID NO: 3 or an expression product of the polynucleotide encoding R2P; hereinafter these may be collectively referred to simply as "R2P") can be determined by competitively reacting an antibody against the polypeptide with labeled R2P in a test liquid containing a test substance, and measuring the amount of the labeled R2P which has been bound to the antibody. Alternatively, the amount of R2P in the test liquid can be determined by reacting the test liquid with an antibody immobilized on a carrier and a different labeled anti-R2P antibody simultaneously or sequentially, and then measuring the activity of a labeling agent on the antibody-immobilized carrier.

According to the screening method of the present invention, binding between R2P and a ligand can be evaluated in, for example, a cell, a cell-free preparation, a chemical library, or a naturally occurring mixture.

An agent for promoting (or enhancing) or inhibiting (or suppressing) the effect of R2P in inhibiting $Ca^{2+}$ leakage, thereby improving abnormal calcium handling (regulation) in cells may be a naturally occurring substrate or ligand, or a structural or functional mimic thereof.

In the screening method of the present invention, a high-throughput screening technique can be applied. With application of this technique, in the case of screening of a $Ca^{2+}$ leakage inhibitor, a $Ca^{2+}$ leakage promoter, or an agent for promoting or inhibiting improvement of abnormal calcium handling (regulation) in the sarcoplasmic reticulum of a cell, a synthesis reaction mixture, a cellular fraction (e.g., endoplasmic reticulum, membrane, cell envelope, or cell wall), or a preparation of any of these (including R2P and a labeled ligand for the polypeptide) is incubated in the presence or absence of a test substance to be screened. Whether the test substance is agonistic or antagonistic to the effects of R2P is determined through detection of reduction of the binding between R2P and the labeled ligand. A test substance which inhibits $Ca^{2+}$ leakage or improves abnormal calcium handling (regulation) without inducing the effects of R2P is highly likely to be a good $Ca^{2+}$ leakage inhibitor or abnormal calcium handling (regulation) improving agent. In contrast, a compound which binds to R2P and increases $Ca^{2+}$ leakage is regarded as an inhibitor against R2P. The activity level of R2P can be detected by means of a reporter system (including, but not limited to, calorimetric labeling), integration of a reporter gene which responds to change in polynucleotide or polypeptide activity, or a binding assay known in the art.

A competitive assay employing R2P, an R2P mutant (MSV-R2P, RP1-20, RP13-32, RP17-36, RP1-30, or RP1-25), or another $Ca^{2+}$ leakage inhibitor (e.g., JTV519, a calcium antagonist such as diltiazem, or a β-blocker such as propranolol) in combination with a compound which binds thereto can be employed for selecting, through screening, a candidate compound serving as a $Ca^{2+}$ leakage inhibitor or promoter, or as an agent for improving or enhancing abnormal calcium handling (regulation).

Test substances (drug candidate compounds) to be screened through the screening method of the present invention include a substance which promotes $Ca^{2+}$ leakage inhibitory activity (in particular, a substance which inhibits $Ca^{2+}$ leakage or a substance which improves abnormal calcium handling (regulation); i.e., agonist), as well as a substance which suppresses $Ca^{2+}$ leakage inhibitory activity (in particular, a substance which promotes $Ca^{2+}$ leakage or a substance which enhances abnormal calcium handling (regulation); i.e., antagonist). In the screening system of the present invention, "agonist" corresponds to a substance which increases $Ca^{2+}$ leakage inhibitory activity to be measured, whereas "antagonist" corresponds to a substance which reduces $Ca^{2+}$ leakage inhibitory activity to be measured.

Specific examples of such a test substance include oligopeptide, protein, antibody, RNA molecule, siRNA, non-peptidic compound (synthetic compound), fermented product, cell extract (e.g., plant extract or animal tissue extract), and plasma. Such a substance may be a newly developed or known substance.

Examples of $Ca^{2+}$ leakage inhibiting substances include an inorganic or organic low-molecular-weight compound which binds to R2P and increases its activity; naturally occurring, synthetic, or genetically modified peptide and polypeptide; and a sense DNA molecule with respect to DNA encoding R2P, which is directly administered in vivo or which is inserted in a recombinant vector for administration.

Examples of $Ca^{2+}$ leakage promoting substances include inorganic or organic low-molecular-weight compound, peptide, polypeptide, antibody, and antisense DNA molecule (see, for example, Okano, J. Neurochem, 56: 560 (1991); and Oligodeoxynucleotides as Antisense Inhibitors of Gene Expression, CRC Press, Boca Raton, Fla. (1988)), each of which does not induce R2P-induced activity ($Ca^{2+}$ leakage inhibitory activity), and can bind to a molecule site to which R2P binds, thereby inhibiting the activity of R2P by preventing binding of R2P to the molecule site, and RNA molecule exhibiting the RNA interference effect (see, for example, McCaffrey, A. P., et al., Nature, 418, 38-39 (2002)).

A candidate substance selected through the screening method of the present invention, which exhibits the effect of promoting or suppressing $Ca^{2+}$ leakage inhibitory activity, can be evaluated as follow. Specifically, when $Ca^{2+}$ leakage inhibitory activity is increased by about 20% or more (preferably about 30% or more, more preferably about 50% or more) as compared with the case of control (in the absence of a test substance), the candidate substance can be selected as a compound which promotes $Ca^{2+}$ leakage inhibitory activity. In contrast, when, for example, $Ca^{2+}$ leakage inhibitory activity is reduced by about 20% or more (preferably about 30% or more, more preferably about 50% or more) as compared with the case of control (in the absence of a test substance), the candidate substance can be selected as a compound which suppresses $Ca^{2+}$ leakage inhibitory activity.

Similar to the case of the invention polypeptide or the invention expression product, a substance selected through the screening method of the present invention and promoting $Ca^{2+}$ leakage inhibitory activity is useful as an active ingredient of a pharmaceutical composition for diseases associated with cellular abnormality resulting from $Ca^{2+}$ leakage or abnormal calcium handling.

Conceivably, a substance selected through the screening method of the present invention and promoting $Ca^{2+}$ leakage inhibitory activity reduces the amount of $Ca^{2+}$ leaked from sarcoplasmic reticulum, to thereby increase $Ca^{2+}$ concentration in the sarcoplasmic reticulum, and to improve abnormal muscle contraction/relaxation function or muscle contraction/relaxation dysfunction in cells. Therefore, a sarcoplasmic reticulum $Ca^{2+}$ increasing agent containing such a substance as an active ingredient is useful in a variety of fields (including the field of pharmaceuticals).

The aforementioned sarcoplasmic reticulum $Ca^{2+}$ increasing agent, an agent for promoting $Ca^{2+}$ leakage inhibitory activity in endoplasmic reticulum, or an agent for improving abnormal calcium handling (regulation) in sarcoplasmic reticulum can be applied to any of the aforementioned diseases in the form of a pharmaceutical composition containing the agent (in an effective amount required for exhibiting its effect) and an appropriate pharmaceutical carrier.

The substance serving as an active ingredient of the pharmaceutical composition; i.e., a sarcoplasmic reticulum $Ca^{2+}$ increasing substance, a substance for promoting $Ca^{2+}$ leakage inhibitory activity in endoplasmic reticulum, or a substance for improving abnormal calcium handling (regulation) in sarcoplasmic reticulum, may be prepared in the form of a pharmaceutically acceptable salt. The type and preparation method of the salt, the preparation method of the pharmaceutical composition, the pharmaceutical carrier (e.g., diluent or excipient) employed in the pharmaceutical composition, the unit dosage form, administration route, and administration method of the pharmaceutical composition, and the like may be similar to those described in detail in the case of the aforementioned pharmaceutical composition containing, as an active ingredient, the invention polypeptide or the invention expression product.

No particular limitation is imposed on the amount of the active ingredient to be contained in the pharmaceutical composition and the dose of the active ingredient, and the amount and the dose are appropriately determined within a wide range in consideration of, for example, the desired therapeutic effect, the administration method, the treatment period, and the age, sex, and other conditions of a patient. The daily dose is generally about 0.01 μg to about 10 mg per kg body weight, preferably about 0.1 μg to about 1 mg per kg body weight. The composition may be administered once daily or in several divided doses per day.

[9] Screening Kit

The present invention also provides a screening kit for selecting an agonist or an antagonist with respect to the $Ca^{2+}$ leakage inhibitory effect of the invention polypeptide or an expression product of the invention polynucleotide in the endoplasmic reticulum of a target cell, which kit is characterized by comprising at least one species selected from the group consisting of the polypeptide and the expression product, which are contained in the target cell, and FK506.

In any embodiment of the screening kit of the present invention, a critical point is to include, as essential components, the invention polypeptide (e.g., a polypeptide having the amino acid sequence of any of SEQ ID NOs: 3 to 9) or the invention expression product (e.g., an expression product of a polynucleotide having the DNA sequence of any of SEQ ID NOs: 20 to 26); and FK506, a substance which induces $Ca^{2+}$ leakage in sarcoplasmic reticulum (i.e., a substance which cuts the bond between ryanodine receptor and FK506-binding protein or promotes phosphorylation of the ryanodine receptor, to thereby induce $Ca^{2+}$ leakage in sarcoplasmic reticulum, to reduce the amount of $Ca^{2+}$ taken into the sarcoplasmic reticulum, and to induce abnormal calcium handling (regulation), resulting in abnormal muscle contraction/relaxation function or muscle contraction/relaxation dysfunction in cells). Other components of the screening kit of the present invention may be similar to those included in a screening kit of this type. For example, the screening kit of the present invention may be a kit including a polypeptide (e.g., R2P) exhibiting the activity of inhibiting $Ca^{2+}$ leakage (improving abnormal calcium handling) in endoplasmic reticulum, and a reagent serving as an optional component, such as a cell culture, a reaction diluent, a dye, a buffer, a fixative, or a detergent.

Specific examples of the screening kit of the present invention include a kit including the following components 1 to 4:

Component 1. Cell preparation obtained through culturing of a target cell (target R2P-expressing cell, which has been prepared through transformation of a cell to be measured with R2P-encoding polynucleotide (DNA molecule)) in a 60-mm dish ($0.5 \times 10^5$ to $1 \times 10^5$ cells/well) at 5% $CO_2$ and 37° C. by use of, for example, MOPS buffer containing EGTA-Ca buffer;

Component 2. Substance which induces $Ca^{2+}$ leakage in endoplasmic reticulum (FK506);

Component 3. Substance which induces calcium uptake (e.g., ATP) and a $Ca^{2+}$ indicator (e.g., fluo3); and Component 4. Calcium ATPase inhibitor (e.g., thapsigargin).

In the screening method employing the screening kit of the present invention, significant difference test can be performed on the amount of change in $Ca^{2+}$ leakage in a target cell as measured per unit visual field of a well to which a test compound (test substance or drug candidate compound) has been added, and on the amount of change in $Ca^{2+}$ leakage in the same cell as measured in a control well to which a test compound has not been added.

The calcium release activity of ryanodine receptor can also be evaluated or detected on the basis of the number of change in channel opening frequency measured through a method other than the aforementioned methods (e.g., a method for measuring the opening frequency by means of single-channel recording) [Reiken, et al., J. Biol. Chem., 278, 444-453 (2003)].

The aforementioned measurement and evaluation can be performed through customary methods.

The present invention will next be described in more detail by way of an Example, which should not be construed as limiting the invention thereto.

EXAMPLE 1

In order to search for a novel substance exhibiting the effect of inhibiting $Ca^{2+}$ leakage in endoplasmic reticulum, firstly, the present inventors synthesized a plurality of polypeptides as therapeutic peptides considered to correct abnormality in RyR2 structure, and searched for a polypeptide exhibiting the effect of inhibiting $Ca^{2+}$ leakage in endoplasmic reticulum.

(a) Polypeptide Synthesis:

Synthesis of polypeptides was performed through solid-phase synthesis employing the Fmoc (9-fluorenylmethyloxycarbonyl) method.

TBTU [2-(1H-benzotriazol-1-yl)-1,1,3,3-tetramethyluronium tetrafluoroborate] and HOBt [1-hydroxybenzotriazole hydrate] were employed as activating reagents, and reaction was performed through a continuous flow system.

The thus-synthesized polypeptides correspond to the following sequences, each having amino acids which are numbered from the N-terminal toward the C-terminal of the amino acid sequence of human ryanodine receptor 2 (hRyR2: GenBank Accession No. NM 001035).

DR3-1: amino acid Nos. 1852-1871 SEQ ID NO: 17
DR3-2: amino acid Nos. 1861-1880 SEQ ID NO: 18
DR3-3: amino acid Nos. 1871-1890 SEQ ID. NO: 19
R22068/87: amino acid Nos. 2068-2087 SEQ ID NO: 13
R2JN28: amino acid Nos. 2086-2113 SEQ ID NO: 14
R2JF: amino acid Nos. 2086-2133 SEQ ID NO: 15
R2P: amino acid Nos. 2114-2149 SEQ ID NO: 3
R22150/85: amino acid Nos. 2150-2185 SEQ ID NO: 16

(b) Measurement of $Ca^{2+}$ Leakage Inhibitory Activity:

$Ca^{2+}$ leakage inhibitory activity was measured through the method of Yano, M., et al. [Yano, et al., Circulation, 102, 2131-2136 (2000)].

Firstly, sarcoplasmic reticulum was prepared from canine myocardium through the method of Kranias, et al. [Kranias E., et al., Biochim. Biophys. Acta., 709, 28-37 (1982)].

Subsequently, the sarcoplasmic reticulum (0.2 mg/mL) was incubated in 0.5 mL of 20 mM MOPS buffer (pH 6.8) containing 0.15 mM potassium gluconate, 0.2 mM EGTA-calcium buffer (free calcium: $Ca^{2+}$=0.3 µM), and 10 mM $NaN_3$.

After the fluorescence value was maintained constant, 0.5 mM ATP (product of Sigma) and 0.5 mM magnesium chloride were added to the resultant mixture, to thereby initiate $Ca^{2+}$ uptake. The time course of $Ca^{2+}$ uptake was measured. $Ca^{2+}$ uptake was measured by means of fluo 3 (product of Molecular Probes) serving as a $Ca^{2+}$ indicator, and the fluorescence intensity at an excitation wavelength of 480 nm and an emission wavelength of 530 nm was measured by means of a fluorometer.

After $Ca^{2+}$ uptake reached a plateau, 1 µM thapsigargin (product of Wako Pure Chemical Industries, Ltd.) was added to thereby inhibit sarco(endo)plasmic reticulum Ca-ATPase (SERCA) activity for elimination of the influence of SERCA. The difference between the fluorescence value before addition of ATP and the fluorescence value at the time of completion of ATP-induced active $Ca^{2+}$ uptake (i.e., the fluorescence value at the time when $Ca^{2+}$ uptake reached a plateau) was taken as 100%. Therefore, when the fluorescence value does not change even if thapsigargin is added, the amount of $Ca^{2+}$ leakage is 0% [it has been reported that $Ca^{2+}$ leakage (about 10 to about 20%) may occur in sarcoplasmic reticulum derived from normal myocardium; Doi, M., et al., Circulation, 105, 1374-1379 (2002)].

$Ca^{2+}$ leakage induced by simultaneous addition of thapsigargin and 30 µM FK506 (product of Fujisawa Pharmaceutical Co., Ltd,), which was regarded as a control of $Ca^{2+}$ leakage induction, was measured by means of a $Ca^{2+}$ indicator.

$Ca^{2+}$ leakage in the case where 0.3 µM JTV-519 (distributed by JT Inc.) exhibiting $Ca^{2+}$ leakage inhibitory activity was added simultaneously with administration of thapsigargin and FK506, which was regarded as a control of $Ca^{2+}$ leakage inhibitory activity, was measured by means of a $Ca^{2+}$ indicator.

A polypeptide obtained in (a) above (concentration: 0.1 µM, 0.3 µM, or 1.0 µM) and FK506 (30 µM/L) were added simultaneously with administration of thapsigargin, and the effect of inhibiting the thus-induced $Ca^{2+}$ leakage via ryanodine receptor was measured by means of a $Ca^{2+}$ indicator in a manner similar to that described above.

Figure 2:
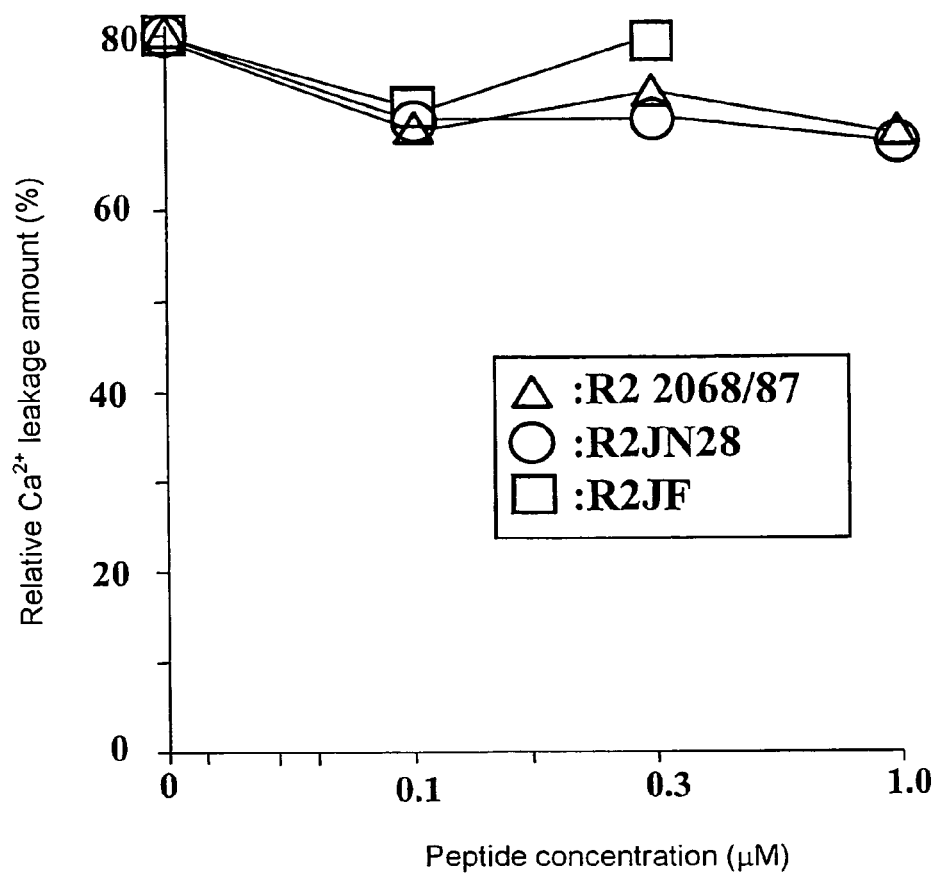
FIG. 2 shows the effects of synthesized polypeptides on FK506-induced $Ca^{2+}$ leakage in the sarcoplasmic reticulum derived from canine myocardium.
Figure 3:
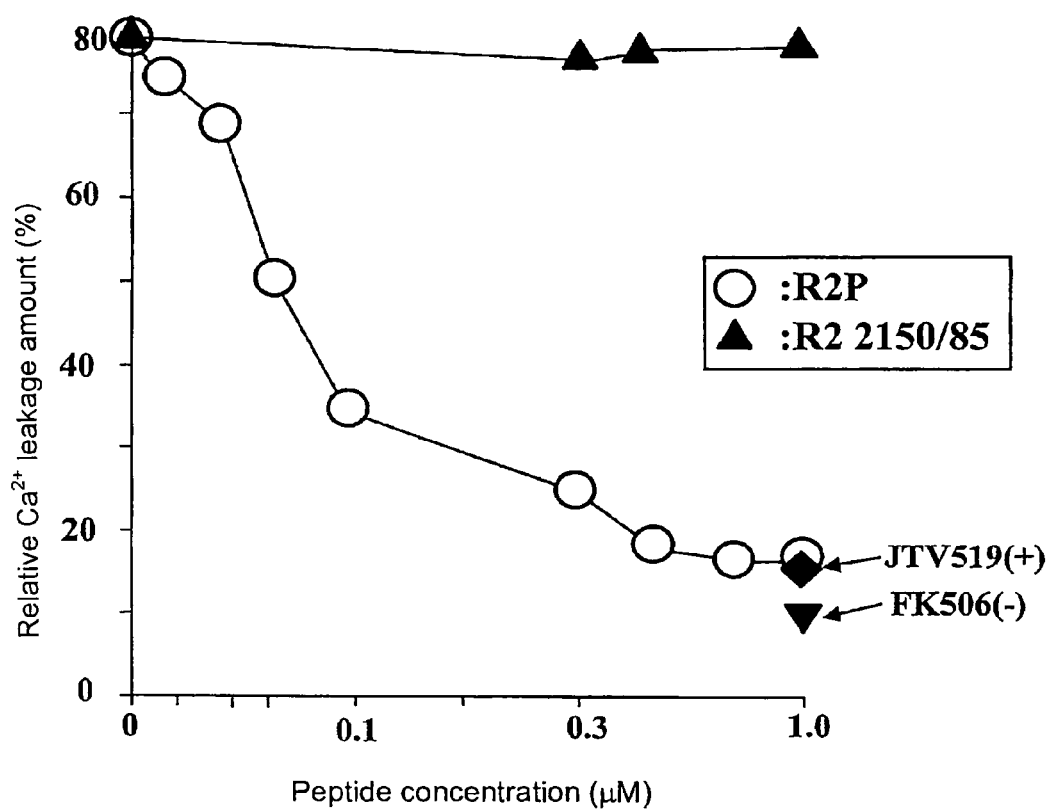
FIG. 3 shows the effects of synthesized polypeptides on FK506-induced $Ca^{2+}$ leakage in the sarcoplasmic reticulum derived from canine myocardium.

The results are shown in FIGS. 1 to 3. In each of these figures, the vertical axis corresponds to the value as measured 20 seconds after addition of thapsigargin, FK506, and a polypeptide. The value is the average of data of measurement performed twice or three times.

As shown in FIGS. 1 to 3, among the above-synthesized polypeptides, R2P, which is represented by SEQ ID NO: 3 corresponding to amino acid Nos. 2114-2149 of human ryanodine receptor 2, inhibits $Ca^{2+}$ leakage in a concentration-dependent manner. In addition, 1.0 µM R2P polypeptide was found to exhibit $Ca^{2+}$ leakage inhibitory effect comparable to that of 0.3 µM JTV519, which is known to exhibit $Ca^{2+}$ leakage inhibitory effect.

(c) Study on $Ca^{2+}$ Leakage Inhibitory Effect of R2P-Related Peptides:

In the aforementioned test, R2P, which is represented by SEQ ID NO: 3 corresponding to amino acid Nos. 2114-2149 of human ryanodine receptor 2, was found to exhibit $Ca^{2+}$ leakage inhibitory effect. Therefore, the present inventors further synthesized peptides having the below-described sequences, which are partial peptides and mutants of R2P. Each of the thus-synthesized peptides was examined whether or not it exhibits $Ca^{2+}$ leakage inhibitory effect.

Figure 4:
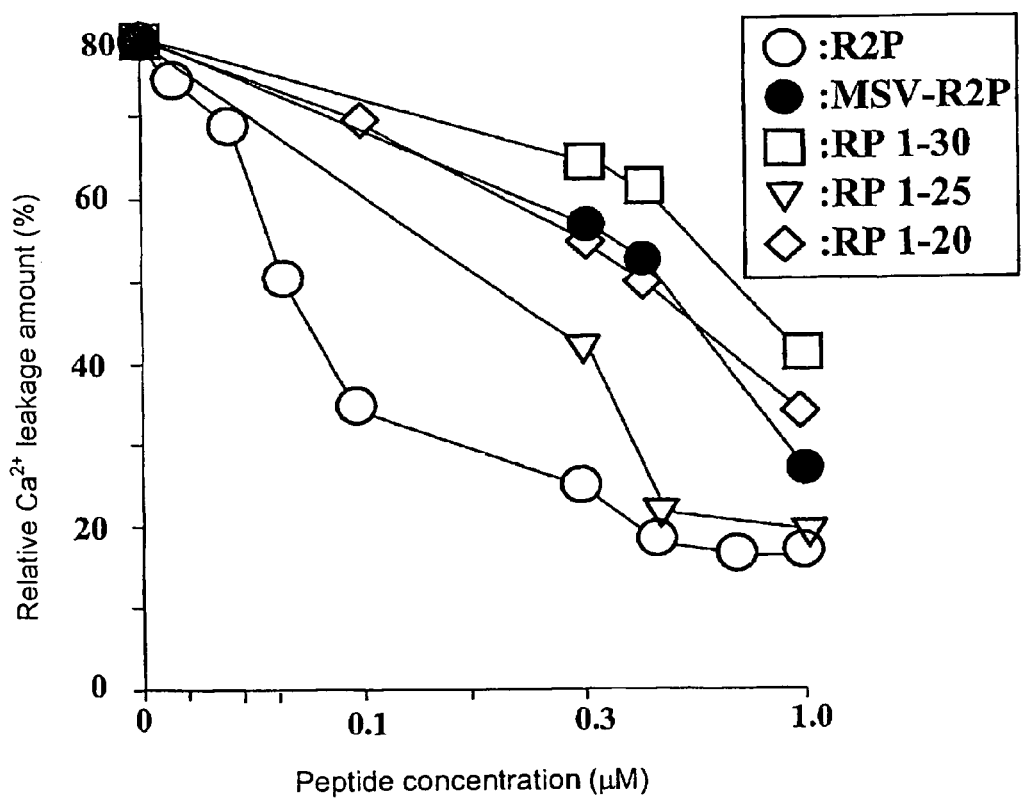
FIG. 4 shows the effects of synthesized polypeptides on FK506-induced $Ca^{2+}$ leakage in the sarcoplasmic reticulum derived from canine myocardium.
Figure 5:
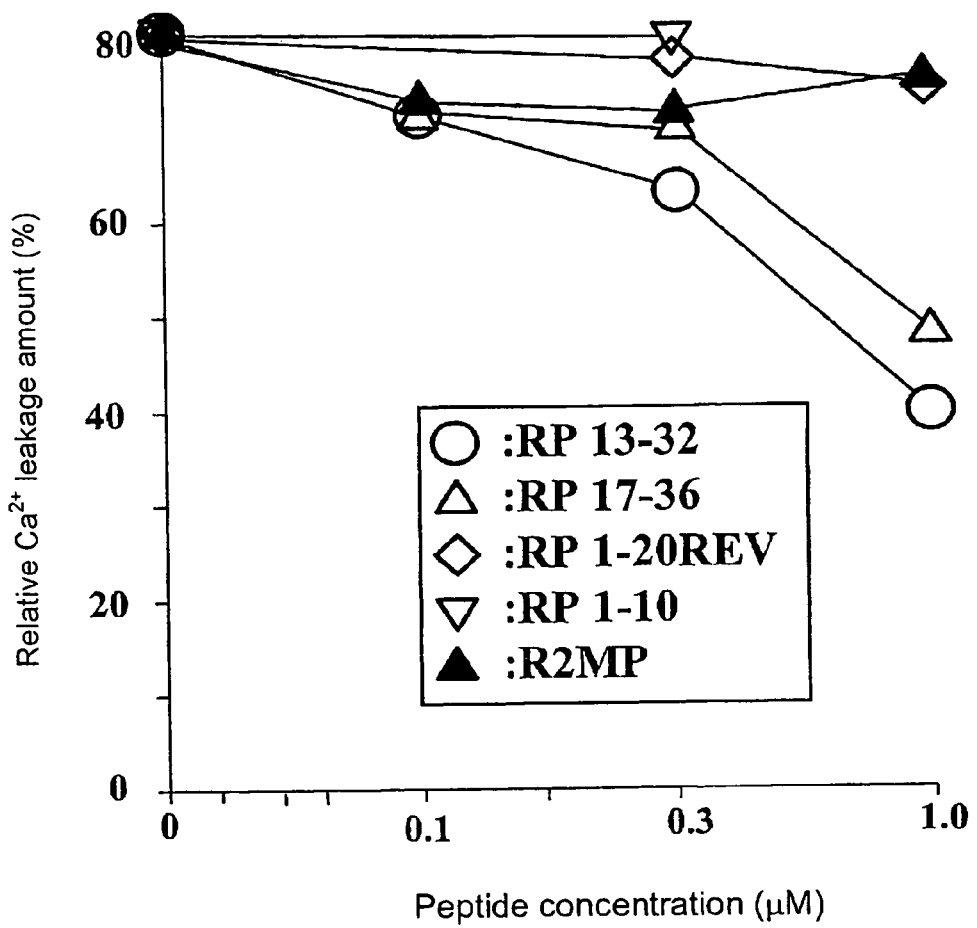
FIG. 5 shows the effects of synthesized polypeptides on FK506-induced $Ca^{2+}$ leakage in the sarcoplasmic reticulum derived from canine myocardium.

Specifically, there were synthesized the following peptides: a peptide (SEQ ID NO: 4) obtained through introduction of three amino acids to the N-terminal of R2P; partial peptides (SEQ ID NOs: 5 to 9 and 11) obtained through deletion of amino acids at the N-terminal, the C-terminal, and both the N- and C-terminals of R2P; a mutant (SEQ ID NO: 12) obtained through substitution of an amino acid of R2P with another amino acid; and a mutant (SEQ ID NO: 10) having a sequence reverse to that of RP1-20. Each of the thus-synthesized peptides was examined in terms of $Ca^{2+}$ leakage inhibitory effect in a manner similar to that described in (b) above. The results are shown in FIGS. 4 and 5.

Synthesized Peptides:
MSV-R2P: amino acid Nos. M+2112-2149 SEQ ID NO: 4
RP1-30: amino acid Nos. 2114-2143 SEQ ID NO: 5
RP1-25: amino acid Nos. 2114-2138 SEQ ID NO: 6
RP1-20: amino acid Nos. 2114-2133 SEQ ID NO: 7
RP13-32: amino acid Nos. 2126-2145 SEQ ID NO: 8
RP17-36: amino acid Nos. 2130-2149 SEQ ID NO: 9
RP1-20REV: amino acid Nos. 2133-2114 SEQ ID NO: 10
RP1-10: amino acid Nos. 2114-2123 SEQ ID NO: 11
R2MP: amino acid Nos. 2114-2149 (V2132M) SEQ ID NO: 12

As a result, the following polypeptides: MSV-RP2 represented by SEQ ID NO: 4, RP1-30 represented by SEQ ID NO: 5, RP1-25 represented by SEQ ID NO: 6, RP1-20 represented by SEQ ID NO: 7, RP13-32 represented by SEQ ID NO: 8, and RP17-36 represented by SEQ ID NO: 9 were found to exhibit $Ca^{2+}$ leakage inhibitory effect in a concentration-dependent manner. However, the $Ca^{2+}$ leakage inhibitory activity of each of the polypeptides was lower than that of R2P.

All the synthesized mutant peptides, the synthesized polypeptides having sequences located upstream and downstream of R2P, and the synthesized polypeptide derived from the DR3 region were found to exhibit no $Ca^{2+}$ leakage inhibitory effect. In addition, the R2JF peptide represented by SEQ ID NO: 15, which had been obtained through introduction, to the N-terminal of R2P 1-20, of the peptide represented by SEQ ID NO: 14 and having no $Ca^{2+}$ leakage inhibitory effect, was found to exhibit no $Ca^{2+}$ leakage inhibitory effect (FIG. 2).

JTV-519 employed as a control is known to inhibit $Ca^{2+}$ leakage from the sarcoplasmic reticulum of failing myocardium in a concentration-dependent manner, to exhibit the effect of improving cardiac function in a tachycardia-induced canine heart failure model, and to exhibit no effect on cardiac function in a normal canine model.

A drug containing, as an active ingredient, the R2P polypeptide of the present invention or a mutant thereof inhibits Ca²⁺ leakage in a concentration-dependent manner, and thus is considered to exhibit effects similar to those of JTV-519. Therefore, the drug can be expected as a therapeutic or preventive agent for a disease whose onset is caused by muscle contraction/relaxation dysfunction due to abnormal calcium handling or induction of Ca²⁺ leakage from sarcoplasmic reticulum.

---

The invention claimed is:

1. A purified polypeptide consisting of the amino acid sequence of SEQ ID NO: 3.

\* \* \* \* \*

SEQUENCE LISTING

<160> NUMBER OF SEQ ID NOS: 26

<210> SEQ ID NO 1
<211> LENGTH: 4967
<212> TYPE: PRT
<213> ORGANISM: Homo sapiens

<400> SEQUENCE: 1

```
Met Ala Asp Gly Gly Glu Gly Glu Asp Glu Ile Gln Phe Leu Arg Thr
1               5                   10                  15

Asp Asp Glu Val Val Leu Gln Cys Thr Ala Thr Ile His Lys Glu Gln
            20                  25                  30

Gln Lys Leu Cys Leu Ala Ala Glu Gly Phe Gly Asn Arg Leu Cys Phe
        35                  40                  45

Leu Glu Ser Thr Ser Asn Ser Lys Asn Val Pro Pro Asp Leu Ser Ile
    50                  55                  60

Cys Thr Phe Val Leu Glu Gln Ser Leu Ser Val Arg Ala Leu Gln Glu
65                  70                  75                  80

Met Leu Ala Asn Thr Val Glu Lys Ser Glu Gly Gln Val Asp Val Glu
                85                  90                  95

Lys Trp Lys Phe Met Met Lys Thr Ala Gln Gly Gly Gly His Arg Thr
            100                 105                 110

Leu Leu Tyr Gly His Ala Ile Leu Leu Arg His Ser Tyr Ser Gly Met
        115                 120                 125

Tyr Leu Cys Cys Leu Ser Thr Ser Arg Ser Ser Thr Asp Lys Leu Ala
    130                 135                 140

Phe Asp Val Gly Leu Gln Glu Asp Thr Thr Gly Glu Ala Cys Trp Trp
145                 150                 155                 160

Thr Ile His Pro Ala Ser Lys Gln Arg Ser Glu Gly Glu Lys Val Arg
                165                 170                 175

Val Gly Asp Asp Leu Ile Leu Val Ser Val Ser Ser Glu Arg Tyr Leu
            180                 185                 190

His Leu Ser Tyr Gly Asn Gly Ser Leu His Val Asp Ala Ala Phe Gln
        195                 200                 205

Gln Thr Leu Trp Ser Val Ala Pro Ile Ser Ser Gly Ser Glu Ala Ala
    210                 215                 220

Gln Gly Tyr Leu Ile Gly Gly Asp Val Leu Arg Leu Leu His Gly His
225                 230                 235                 240

Met Asp Glu Cys Leu Thr Val Pro Ser Gly Glu His Gly Glu Glu Gln
                245                 250                 255

Arg Arg Thr Val His Tyr Glu Gly Gly Ala Val Ser Val His Ala Arg
            260                 265                 270

Ser Leu Trp Arg Leu Glu Thr Leu Arg Val Ala Trp Ser Gly Ser His
        275                 280                 285

Ile Arg Trp Gly Gln Pro Phe Arg Leu Arg His Val Thr Thr Gly Lys
    290                 295                 300

Tyr Leu Ser Leu Met Glu Asp Lys Asn Leu Leu Leu Met Asp Lys Glu
305                 310                 315                 320
```

```
Lys Ala Asp Val Lys Ser Thr Ala Phe Thr Phe Arg Ser Ser Lys Glu
            325                 330                 335

Lys Leu Asp Val Gly Val Arg Lys Glu Val Asp Gly Met Gly Thr Ser
            340                 345                 350

Glu Ile Lys Tyr Gly Asp Ser Val Cys Tyr Ile Gln His Val Asp Thr
            355                 360                 365

Gly Leu Trp Leu Thr Tyr Gln Ser Val Asp Val Lys Ser Val Arg Met
        370                 375                 380

Gly Ser Ile Gln Arg Lys Ala Ile Met His His Glu Gly His Met Asp
385                 390                 395                 400

Asp Gly Ile Ser Leu Ser Arg Ser Gln His Glu Glu Ser Arg Thr Ala
                405                 410                 415

Arg Val Ile Arg Ser Thr Val Phe Leu Phe Asn Arg Phe Ile Arg Gly
                420                 425                 430

Leu Asp Ala Leu Ser Lys Lys Ala Lys Ala Ser Thr Val Asp Leu Pro
            435                 440                 445

Ile Glu Ser Val Ser Leu Ser Leu Gln Asp Leu Ile Gly Tyr Phe His
        450                 455                 460

Pro Pro Asp Glu His Leu Glu His Glu Asp Lys Gln Asn Arg Leu Arg
465                 470                 475                 480

Ala Leu Lys Asn Arg Gln Asn Leu Phe Gln Glu Gly Met Ile Asn
                485                 490                 495

Leu Val Leu Glu Cys Ile Asp Arg Leu His Val Tyr Ser Ser Ala Ala
                500                 505                 510

His Phe Ala Asp Val Ala Gly Arg Glu Ala Gly Glu Ser Trp Lys Ser
            515                 520                 525

Ile Leu Asn Ser Leu Tyr Glu Leu Leu Ala Ala Leu Ile Arg Gly Asn
        530                 535                 540

Arg Lys Asn Cys Ala Gln Phe Ser Gly Ser Leu Asp Trp Leu Ile Ser
545                 550                 555                 560

Arg Leu Glu Arg Leu Glu Ala Ser Ser Gly Ile Leu Glu Val Leu His
                565                 570                 575

Cys Val Leu Val Glu Ser Pro Glu Ala Leu Asn Ile Ile Lys Glu Gly
            580                 585                 590

His Ile Lys Ser Ile Ile Ser Leu Leu Asp Lys His Gly Arg Asn His
        595                 600                 605

Lys Val Leu Asp Val Leu Cys Ser Leu Cys Val Cys His Gly Val Ala
    610                 615                 620

Val Arg Ser Asn Gln His Leu Ile Cys Asp Asn Leu Leu Pro Gly Arg
625                 630                 635                 640

Asp Leu Leu Leu Gln Thr Arg Leu Val Asn His Val Ser Ser Met Arg
                645                 650                 655

Pro Asn Ile Phe Leu Gly Val Ser Glu Gly Ser Ala Gln Tyr Lys Lys
                660                 665                 670

Trp Tyr Tyr Glu Leu Met Val Asp His Thr Glu Pro Phe Val Thr Ala
        675                 680                 685

Glu Ala Thr His Leu Arg Val Gly Trp Ala Ser Thr Glu Gly Tyr Ser
            690                 695                 700

Pro Tyr Pro Gly Gly Gly Glu Glu Trp Gly Gly Asn Gly Val Gly Asp
705                 710                 715                 720

Asp Leu Phe Ser Tyr Gly Phe Asp Gly Leu His Leu Trp Ser Gly Cys
            725                 730                 735

Ile Ala Arg Thr Val Ser Ser Pro Asn Gln His Leu Leu Arg Thr Asp
```

-continued

```
                740               745               750
Asp Val Ile Ser Cys Cys Leu Asp Leu Ser Ala Pro Ser Ile Ser Phe
                    755               760               765
Arg Ile Asn Gly Gln Pro Val Gln Gly Met Phe Glu Asn Phe Asn Ile
770               775               780
Asp Gly Leu Phe Phe Pro Val Ser Phe Ser Ala Gly Ile Lys Val
785               790               795               800
Arg Phe Leu Leu Gly Gly Arg His Gly Glu Phe Lys Phe Leu Pro Pro
                    805               810               815
Pro Gly Tyr Ala Pro Cys Tyr Glu Ala Val Leu Pro Lys Glu Lys Leu
            820               825               830
Lys Val Glu His Ser Arg Glu Tyr Lys Gln Glu Arg Thr Tyr Thr Arg
                835               840               845
Asp Leu Leu Gly Pro Thr Val Ser Leu Thr Gln Ala Ala Phe Thr Pro
850               855               860
Ile Pro Val Asp Thr Ser Gln Ile Val Leu Pro His Leu Glu Arg
865               870               875               880
Ile Arg Glu Lys Leu Ala Glu Asn Ile His Glu Leu Trp Val Met Asn
                    885               890               895
Lys Ile Glu Leu Gly Trp Gln Tyr Gly Pro Val Arg Asp Asp Asn Lys
                900               905               910
Arg Gln His Pro Cys Leu Val Glu Phe Ser Lys Leu Pro Glu Gln Glu
            915               920               925
Arg Asn Tyr Asn Leu Gln Met Ser Leu Glu Thr Leu Lys Thr Leu Leu
        930               935               940
Ala Leu Gly Cys His Val Gly Ile Ser Asp Glu His Ala Glu Asp Lys
945               950               955               960
Val Lys Lys Met Lys Leu Pro Lys Asn Tyr Gln Leu Thr Ser Gly Tyr
                965               970               975
Lys Pro Ala Pro Met Asp Leu Ser Phe Ile Lys Leu Thr Pro Ser Gln
                980               985               990
Glu Ala Met Val Asp Lys Leu Ala  Glu Asn Ala His Asn  Val Trp Ala
            995               1000              1005
Arg Asp Arg Ile Arg Gln Gly  Trp Thr Tyr Gly Ile  Gln Gln Asp
    1010              1015              1020
Val Lys  Asn Arg Arg Asn Pro  Arg Leu Val Pro Tyr  Thr Pro Leu
    1025              1030              1035
Asp Asp  Arg Thr Lys Lys Ser  Asn Lys Asp Ser Leu  Arg Glu Ala
    1040              1045              1050
Val Arg  Thr Leu Leu Gly Tyr  Gly Tyr Asn Leu Glu  Ala Pro Asp
    1055              1060              1065
Gln Asp  His Ala Ala Arg Ala  Glu Val Cys Ser Gly  Thr Gly Glu
    1070              1075              1080
Arg Phe  Arg Ile Phe Arg Ala  Glu Lys Thr Tyr Ala  Val Lys Ala
    1085              1090              1095
Gly Arg  Trp Tyr Phe Glu Phe  Glu Thr Val Thr Ala  Gly Asp Met
    1100              1105              1110
Arg Val  Gly Trp Ser Arg Pro  Gly Cys Gln Pro Asp  Gln Glu Leu
    1115              1120              1125
Gly Ser  Asp Glu Arg Ala Phe  Ala Phe Asp Gly Phe  Lys Ala Gln
    1130              1135              1140
Arg Trp  His Gln Gly Asn Glu  His Tyr Gly Arg Ser  Trp Gln Ala
    1145              1150              1155
```

-continued

Gly Asp Val Val Gly Cys Met Val Asp Met Asn Glu His Thr Met
1160            1165                1170

Met Phe Thr Leu Asn Gly Glu Ile Leu Leu Asp Asp Ser Gly Ser
1175            1180                1185

Glu Leu Ala Phe Lys Asp Phe Asp Val Gly Asp Gly Phe Ile Pro
1190            1195                1200

Val Cys Ser Leu Gly Val Ala Gln Val Gly Arg Met Asn Phe Gly
1205            1210                1215

Lys Asp Val Ser Thr Leu Lys Tyr Phe Thr Ile Cys Gly Leu Gln
1220            1225                1230

Glu Gly Tyr Glu Pro Phe Ala Val Asn Thr Asn Arg Asp Ile Thr
1235            1240                1245

Met Trp Leu Ser Lys Arg Leu Pro Gln Phe Leu Gln Val Pro Ser
1250            1255                1260

Asn His Glu His Ile Glu Val Thr Arg Ile Asp Gly Thr Ile Asp
1265            1270                1275

Ser Ser Pro Cys Leu Lys Val Thr Gln Lys Ser Phe Gly Ser Gln
1280            1285                1290

Asn Ser Asn Thr Asp Ile Met Phe Tyr Arg Leu Ser Met Pro Ile
1295            1300                1305

Glu Cys Ala Glu Val Phe Ser Lys Thr Val Ala Gly Gly Leu Pro
1310            1315                1320

Gly Ala Gly Leu Phe Gly Pro Lys Asn Asp Leu Glu Asp Tyr Asp
1325            1330                1335

Ala Asp Ser Asp Phe Glu Val Leu Met Lys Thr Ala His Gly His
1340            1345                1350

Leu Val Pro Asp Arg Val Asp Lys Asp Lys Glu Ala Thr Lys Pro
1355            1360                1365

Glu Phe Asn Asn His Lys Asp Tyr Ala Gln Glu Lys Pro Ser Arg
1370            1375                1380

Leu Lys Gln Arg Phe Leu Leu Arg Arg Thr Lys Pro Asp Tyr Ser
1385            1390                1395

Thr Ser His Ser Ala Arg Leu Thr Glu Asp Val Leu Ala Asp Asp
1400            1405                1410

Arg Asp Asp Tyr Asp Phe Leu Met Gln Thr Ser Thr Tyr Tyr Tyr
1415            1420                1425

Ser Val Arg Ile Phe Pro Gly Gln Glu Pro Ala Asn Val Trp Val
1430            1435                1440

Gly Trp Ile Thr Ser Asp Phe His Gln Tyr Asp Thr Gly Phe Asp
1445            1450                1455

Leu Asp Arg Val Arg Thr Val Thr Val Thr Leu Gly Asp Glu Lys
1460            1465                1470

Gly Lys Val His Glu Ser Ile Lys Arg Ser Asn Cys Tyr Met Val
1475            1480                1485

Cys Ala Gly Glu Ser Met Ser Pro Gly Gln Gly Arg Asn Asn Asn
1490            1495                1500

Gly Leu Glu Ile Gly Cys Val Val Asp Ala Ala Ser Gly Leu Leu
1505            1510                1515

Thr Phe Ile Ala Asn Gly Lys Glu Leu Ser Thr Tyr Tyr Gln Val
1520            1525                1530

Glu Pro Ser Thr Lys Leu Phe Pro Ala Val Phe Ala Gln Ala Thr
1535            1540                1545

-continued

```
Ser Pro Asn Val Phe Gln Phe Glu Leu Gly Arg Ile Lys Asn Val
    1550                1555                1560

Met Pro Leu Ser Ala Gly Leu Phe Lys Ser Glu His Lys Asn Pro
    1565                1570                1575

Val Pro Gln Cys Pro Pro Arg Leu His Val Gln Phe Leu Ser His
    1580                1585                1590

Val Leu Trp Ser Arg Met Pro Asn Gln Phe Leu Lys Val Asp Val
    1595                1600                1605

Ser Arg Ile Ser Glu Arg Gln Gly Trp Leu Val Gln Cys Leu Asp
    1610                1615                1620

Pro Leu Gln Phe Met Ser Leu His Ile Pro Glu Glu Asn Arg Ser
    1625                1630                1635

Val Asp Ile Leu Glu Leu Thr Glu Gln Glu Glu Leu Leu Lys Phe
    1640                1645                1650

His Tyr His Thr Leu Arg Leu Tyr Ser Ala Val Cys Ala Leu Gly
    1655                1660                1665

Asn His Arg Val Ala His Ala Leu Cys Ser His Val Asp Glu Pro
    1670                1675                1680

Gln Leu Leu Tyr Ala Ile Glu Asn Lys Tyr Met Pro Gly Leu Leu
    1685                1690                1695

Arg Ala Gly Tyr Tyr Asp Leu Leu Ile Asp Ile His Leu Ser Ser
    1700                1705                1710

Tyr Ala Thr Ala Arg Leu Met Met Asn Asn Glu Tyr Ile Val Pro
    1715                1720                1725

Met Thr Glu Glu Thr Lys Ser Ile Thr Leu Phe Pro Asp Glu Asn
    1730                1735                1740

Lys Lys His Gly Leu Pro Gly Ile Gly Leu Ser Thr Ser Leu Arg
    1745                1750                1755

Pro Arg Met Gln Phe Ser Ser Pro Ser Phe Val Ser Ile Ser Asn
    1760                1765                1770

Glu Cys Tyr Gln Tyr Ser Pro Glu Phe Pro Leu Asp Ile Leu Lys
    1775                1780                1785

Ser Lys Thr Ile Gln Met Leu Thr Glu Ala Val Lys Glu Gly Ser
    1790                1795                1800

Leu His Ala Arg Asp Pro Val Gly Gly Thr Thr Glu Phe Leu Phe
    1805                1810                1815

Val Pro Leu Ile Lys Leu Phe Tyr Thr Leu Leu Ile Met Gly Ile
    1820                1825                1830

Phe His Asn Glu Asp Leu Lys His Ile Leu Gln Leu Ile Glu Pro
    1835                1840                1845

Ser Val Phe Lys Glu Ala Ala Thr Pro Glu Glu Ser Asp Thr
    1850                1855                1860

Leu Glu Lys Glu Leu Ser Val Asp Asp Ala Lys Leu Gln Gly Ala
    1865                1870                1875

Gly Glu Glu Glu Ala Lys Gly Gly Lys Arg Pro Lys Glu Gly Leu
    1880                1885                1890

Leu Gln Met Lys Leu Pro Glu Pro Val Lys Leu Gln Met Cys Leu
    1895                1900                1905

Leu Leu Gln Tyr Leu Cys Asp Cys Gln Val Arg His Arg Ile Glu
    1910                1915                1920

Ala Ile Val Ala Phe Ser Asp Asp Phe Val Ala Lys Leu Gln Asp
    1925                1930                1935

Asn Gln Arg Phe Arg Tyr Asn Glu Val Met Gln Ala Leu Asn Met
```

|  |  |  |  |  |  |  |  |  |  |
|---|---|---|---|---|---|---|---|---|---|
| | 1940 | | | 1945 | | | 1950 | | |
| Ser 1955 | Ala | Ala | Leu | Thr 1960 | Ala | Arg | Lys | Thr 1965 | Lys | Glu | Phe | Arg | Ser | Pro |
| Pro 1970 | Gln | Glu | Gln | Ile 1975 | Asn | Met | Leu | Leu 1980 | Asn | Phe | Lys | Asp | Asp | Lys |
| Ser 1985 | Glu | Cys | Pro | Cys 1990 | Pro | Glu | Glu | Ile 1995 | Arg | Asp | Gln | Leu | Leu | Asp |
| Phe 2000 | His | Glu | Asp | Leu 2005 | Met | Thr | His | Cys 2010 | Gly | Ile | Glu | Leu | Asp | Glu |
| Asp 2015 | Gly | Ser | Leu | Asp 2020 | Gly | Asn | Ser | Asp 2025 | Leu | Thr | Ile | Arg | Gly | Arg |
| Leu 2030 | Leu | Ser | Leu | Val 2035 | Glu | Lys | Val | Thr 2040 | Tyr | Leu | Lys | Lys | Lys | Gln |
| Ala 2045 | Glu | Lys | Pro | Val 2050 | Glu | Ser | Asp | Ser 2055 | Lys | Lys | Ser | Ser | Thr | Leu |
| Gln 2060 | Gln | Leu | Ile | Ser 2065 | Glu | Thr | Met | Val 2070 | Arg | Trp | Ala | Gln | Glu | Ser |
| Val 2075 | Ile | Glu | Asp | Pro 2080 | Glu | Leu | Val | Arg 2085 | Ala | Met | Phe | Val | Leu | Leu |
| His 2090 | Arg | Gln | Tyr | Asp 2095 | Gly | Ile | Gly | Gly 2100 | Leu | Val | Arg | Ala | Leu | Pro |
| Lys 2105 | Thr | Tyr | Thr | Ile 2110 | Asn | Gly | Val | Ser 2115 | Val | Glu | Asp | Thr | Ile | Asn |
| Leu 2120 | Leu | Ala | Ser | Leu 2125 | Gly | Gln | Ile | Arg 2130 | Ser | Leu | Leu | Ser | Val | Arg |
| Met 2135 | Gly | Lys | Glu | Glu 2140 | Lys | Leu | Met | Ile 2145 | Arg | Gly | Leu | Gly | Asp |
| Ile 2150 | Met | Asn | Asn | Lys 2155 | Val | Phe | Tyr | Gln 2160 | His | Pro | Asn | Leu | Met | Arg |
| Ala 2165 | Leu | Gly | Met | His 2170 | Glu | Thr | Val | Met 2175 | Glu | Val | Met | Val | Asn | Val |
| Leu 2180 | Gly | Gly | Gly | Glu 2185 | Ser | Lys | Glu | Ile 2190 | Thr | Phe | Pro | Lys | Met | Val |
| Ala 2195 | Asn | Cys | Cys | Arg 2200 | Phe | Leu | Cys | Tyr 2205 | Phe | Cys | Arg | Ile | Ser | Arg |
| Gln 2210 | Asn | Gln | Lys | Ala 2215 | Met | Phe | Asp | His 2220 | Leu | Ser | Tyr | Leu | Leu | Glu |
| Asn 2225 | Ser | Ser | Val | Gly 2230 | Leu | Ala | Ser | Pro 2235 | Ala | Met | Arg | Gly | Ser | Thr |
| Pro 2240 | Leu | Asp | Val | Ala 2245 | Ala | Ala | Ser | Val 2250 | Met | Asp | Asn | Asn | Glu | Leu |
| Ala 2255 | Leu | Ala | Leu | Arg 2260 | Glu | Pro | Asp | Leu 2265 | Glu | Lys | Val | Val | Arg | Tyr |
| Leu 2270 | Ala | Gly | Cys | Gly 2275 | Leu | Gln | Ser | Cys 2280 | Gln | Met | Leu | Val | Ser | Lys |
| Gly 2285 | Tyr | Pro | Asp | Ile 2290 | Gly | Trp | Asn | Pro 2295 | Val | Glu | Gly | Glu | Arg | Tyr |
| Leu 2300 | Asp | Phe | Leu | Arg 2305 | Phe | Ala | Val | Phe 2310 | Cys | Asn | Gly | Glu | Ser | Val |
| Glu 2315 | Glu | Asn | Ala | Asn 2320 | Val | Val | Val | Arg 2325 | Leu | Leu | Ile | Arg | Arg | Pro |
| Glu 2330 | Cys | Phe | Gly | Pro 2335 | Ala | Leu | Arg | Gly 2340 | Glu | Gly | Gly | Asn | Gly | Leu |

-continued

```
Leu Ala Ala Met Glu Glu Ala Ile Lys Ile Ala Glu Asp Pro Ser
2345                2350                2355

Arg Asp Gly Pro Ser Pro Asn Ser Gly Ser Ser Lys Thr Leu Asp
2360                2365                2370

Thr Glu Glu Glu Asp Asp Thr Ile His Met Gly Asn Ala Ile
2375                2380                2385

Met Thr Phe Tyr Ser Ala Leu Ile Asp Leu Leu Gly Arg Cys Ala
2390                2395                2400

Pro Glu Met His Leu Ile His Ala Gly Lys Gly Glu Ala Ile Arg
2405                2410                2415

Ile Arg Ser Ile Leu Arg Ser Leu Ile Pro Leu Gly Asp Leu Val
2420                2425                2430

Gly Val Ile Ser Ile Ala Phe Gln Met Pro Thr Ile Ala Lys Asp
2435                2440                2445

Gly Asn Val Val Glu Pro Asp Met Ser Ala Gly Phe Cys Pro Asp
2450                2455                2460

His Lys Ala Ala Met Val Leu Phe Leu Asp Arg Val Tyr Gly Ile
2465                2470                2475

Glu Val Gln Asp Phe Leu Leu His Leu Leu Glu Val Gly Phe Leu
2480                2485                2490

Pro Asp Leu Arg Ala Ala Ala Ser Leu Asp Thr Ala Ala Leu Ser
2495                2500                2505

Ala Thr Asp Met Ala Leu Ala Leu Asn Arg Tyr Leu Cys Thr Ala
2510                2515                2520

Val Leu Pro Leu Leu Thr Arg Cys Ala Pro Leu Phe Ala Gly Thr
2525                2530                2535

Glu His His Ala Ser Leu Ile Asp Ser Leu Leu His Thr Val Tyr
2540                2545                2550

Arg Leu Ser Lys Gly Cys Ser Leu Thr Lys Ala Gln Arg Asp Ser
2555                2560                2565

Ile Glu Val Cys Leu Leu Ser Ile Cys Gly Gln Leu Arg Pro Ser
2570                2575                2580

Met Met Gln His Leu Leu Arg Arg Leu Val Phe Asp Val Pro Leu
2585                2590                2595

Leu Asn Glu His Ala Lys Met Pro Leu Lys Leu Leu Thr Asn His
2600                2605                2610

Tyr Glu Arg Cys Trp Lys Tyr Tyr Cys Leu Pro Gly Gly Trp Gly
2615                2620                2625

Asn Phe Gly Ala Ala Ser Glu Glu Glu Leu His Leu Ser Arg Lys
2630                2635                2640

Leu Phe Trp Gly Ile Phe Asp Ala Leu Ser Gln Lys Lys Tyr Glu
2645                2650                2655

Gln Glu Leu Phe Lys Leu Ala Leu Pro Cys Leu Ser Ala Val Ala
2660                2665                2670

Gly Ala Leu Pro Pro Asp Tyr Met Glu Ser Asn Tyr Val Ser Met
2675                2680                2685

Met Glu Lys Gln Ser Ser Met Asp Ser Glu Gly Asn Phe Asn Pro
2690                2695                2700

Gln Pro Val Asp Thr Ser Asn Ile Thr Ile Pro Glu Lys Leu Glu
2705                2710                2715

Tyr Phe Ile Asn Lys Tyr Ala Glu His Ser His Asp Lys Trp Ser
2720                2725                2730
```

-continued

Met Asp Lys Leu Ala Asn Gly Trp Ile Tyr Gly Glu Ile Tyr Ser
2735                2740                2745

Asp Ser Ser Lys Val Gln Pro Leu Met Lys Pro Tyr Lys Leu Leu
    2750                2755                2760

Ser Glu Lys Glu Lys Glu Ile Tyr Arg Trp Pro Ile Lys Glu Ser
2765                2770                2775

Leu Lys Thr Met Leu Ala Arg Thr Met Arg Thr Glu Arg Thr Arg
    2780                2785                2790

Glu Gly Asp Ser Met Ala Leu Tyr Asn Arg Thr Arg Arg Ile Ser
2795                2800                2805

Gln Thr Ser Gln Val Ser Val Asp Ala Ala His Gly Tyr Ser Pro
    2810                2815                2820

Arg Ala Ile Asp Met Ser Asn Val Thr Leu Ser Arg Asp Leu His
2825                2830                2835

Ala Met Ala Glu Met Met Ala Glu Asn Tyr His Asn Ile Trp Ala
    2840                2845                2850

Lys Lys Lys Lys Met Glu Leu Glu Ser Lys Gly Gly Gly Asn His
2855                2860                2865

Pro Leu Leu Val Pro Tyr Asp Thr Leu Thr Ala Lys Glu Lys Ala
    2870                2875                2880

Lys Asp Arg Glu Lys Ala Gln Asp Ile Leu Lys Phe Leu Gln Ile
2885                2890                2895

Asn Gly Tyr Ala Val Ser Arg Gly Phe Lys Asp Leu Glu Leu Asp
    2900                2905                2910

Thr Pro Ser Ile Glu Lys Arg Phe Ala Tyr Ser Phe Leu Gln Gln
2915                2920                2925

Leu Ile Arg Tyr Val Asp Glu Ala His Gln Tyr Ile Leu Glu Phe
    2930                2935                2940

Asp Gly Gly Ser Arg Gly Lys Gly Glu His Phe Pro Tyr Glu Gln
2945                2950                2955

Glu Ile Lys Phe Phe Ala Lys Val Val Leu Pro Leu Ile Asp Gln
    2960                2965                2970

Tyr Phe Lys Asn His Arg Leu Tyr Phe Leu Ser Ala Ala Ser Arg
2975                2980                2985

Pro Leu Cys Ser Gly Gly His Ala Ser Asn Lys Glu Lys Glu Met
    2990                2995                3000

Val Thr Ser Leu Phe Cys Lys Leu Gly Val Leu Val Arg His Arg
3005                3010                3015

Ile Ser Leu Phe Gly Asn Asp Ala Thr Ser Ile Val Asn Cys Leu
    3020                3025                3030

His Ile Leu Gly Gln Thr Leu Asp Ala Arg Thr Val Met Lys Thr
3035                3040                3045

Gly Leu Glu Ser Val Lys Ser Ala Leu Arg Ala Phe Leu Asp Asn
    3050                3055                3060

Ala Ala Glu Asp Leu Glu Lys Thr Met Glu Asn Leu Lys Gln Gly
3065                3070                3075

Gln Phe Thr His Thr Arg Asn Gln Pro Lys Gly Val Thr Gln Ile
    3080                3085                3090

Ile Asn Tyr Thr Thr Val Ala Leu Leu Pro Met Leu Ser Ser Leu
3095                3100                3105

Phe Glu His Ile Gly Gln His Gln Phe Gly Glu Asp Leu Ile Leu
    3110                3115                3120

Glu Asp Val Gln Val Ser Cys Tyr Arg Ile Leu Thr Ser Leu Tyr

```
                    3125                3130                3135

Ala Leu Gly Thr Ser Lys Ser Ile Tyr Val Glu Arg Gln Arg Ser
    3140                3145                3150

Ala Leu Gly Glu Cys Leu Ala Ala Phe Ala Gly Ala Phe Pro Val
    3155                3160                3165

Ala Phe Leu Glu Thr His Leu Asp Lys His Asn Ile Tyr Ser Ile
    3170                3175                3180

Tyr Asn Thr Lys Ser Ser Arg Glu Arg Ala Ala Leu Ser Leu Pro
    3185                3190                3195

Thr Asn Val Glu Asp Val Cys Pro Asn Ile Pro Ser Leu Glu Lys
    3200                3205                3210

Leu Met Glu Glu Ile Val Glu Leu Ala Glu Ser Gly Ile Arg Tyr
    3215                3220                3225

Thr Gln Met Pro His Val Met Glu Val Ile Leu Pro Met Leu Cys
    3230                3235                3240

Ser Tyr Met Ser Arg Trp Trp Glu His Gly Pro Glu Asn Asn Pro
    3245                3250                3255

Glu Arg Ala Glu Met Cys Cys Thr Ala Leu Asn Ser Glu His Met
    3260                3265                3270

Asn Thr Leu Leu Gly Asn Ile Leu Lys Ile Ile Tyr Asn Asn Leu
    3275                3280                3285

Gly Ile Asp Glu Gly Ala Trp Met Lys Arg Leu Ala Val Phe Ser
    3290                3295                3300

Gln Pro Ile Ile Asn Lys Val Lys Pro Gln Leu Leu Lys Thr His
    3305                3310                3315

Phe Leu Pro Leu Met Glu Lys Leu Lys Lys Lys Ala Ala Thr Val
    3320                3325                3330

Val Ser Glu Glu Asp His Leu Lys Ala Glu Ala Arg Gly Asp Met
    3335                3340                3345

Ser Glu Ala Glu Leu Leu Ile Leu Asp Glu Phe Thr Thr Leu Ala
    3350                3355                3360

Arg Asp Leu Tyr Ala Phe Tyr Pro Leu Leu Ile Arg Phe Val Asp
    3365                3370                3375

Tyr Asn Arg Ala Lys Trp Leu Lys Glu Pro Asn Pro Glu Ala Glu
    3380                3385                3390

Glu Leu Phe Arg Met Val Ala Glu Val Phe Ile Tyr Trp Ser Lys
    3395                3400                3405

Ser His Asn Phe Lys Arg Glu Glu Gln Asn Phe Val Val Gln Asn
    3410                3415                3420

Glu Ile Asn Asn Met Ser Phe Leu Ile Thr Asp Thr Lys Ser Lys
    3425                3430                3435

Met Ser Lys Ala Ala Val Ser Asp Gln Glu Arg Lys Lys Met Lys
    3440                3445                3450

Arg Lys Gly Asp Arg Tyr Ser Met Gln Thr Ser Leu Ile Val Ala
    3455                3460                3465

Ala Leu Lys Arg Leu Leu Pro Ile Gly Leu Asn Ile Cys Ala Pro
    3470                3475                3480

Gly Asp Gln Glu Leu Ile Ala Leu Ala Lys Asn Arg Phe Ser Leu
    3485                3490                3495

Lys Asp Thr Glu Asp Glu Val Arg Asp Ile Ile Arg Ser Asn Ile
    3500                3505                3510

His Leu Gln Gly Lys Leu Glu Asp Pro Ala Ile Arg Trp Gln Met
    3515                3520                3525
```

```
Ala Leu Tyr Lys Asp Leu Pro Asn Arg Thr Asp Thr Ser Asp
    3530                3535                3540

Pro Glu Lys Thr Val Glu Arg Val Leu Asp Ile Ala Asn Val Leu
    3545                3550                3555

Phe His Leu Glu Gln Lys Ser Lys Arg Val Gly Arg Arg His Tyr
    3560                3565                3570

Cys Leu Val Glu His Pro Gln Arg Ser Lys Lys Ala Val Trp His
    3575                3580                3585

Lys Leu Leu Ser Lys Gln Arg Lys Arg Ala Val Val Ala Cys Phe
    3590                3595                3600

Arg Met Ala Pro Leu Tyr Asn Leu Pro Arg His Arg Ala Val Asn
    3605                3610                3615

Leu Phe Leu Gln Gly Tyr Glu Lys Ser Trp Ile Glu Thr Glu Glu
    3620                3625                3630

His Tyr Phe Glu Asp Lys Leu Ile Glu Asp Leu Ala Lys Pro Gly
    3635                3640                3645

Ala Glu Pro Pro Glu Glu Asp Glu Gly Thr Lys Arg Val Asp Pro
    3650                3655                3660

Leu His Gln Leu Ile Leu Leu Phe Ser Arg Thr Ala Leu Thr Glu
    3665                3670                3675

Lys Cys Lys Leu Glu Glu Asp Phe Leu Tyr Met Ala Tyr Ala Asp
    3680                3685                3690

Ile Met Ala Lys Ser Cys His Asp Glu Glu Asp Asp Gly Glu
    3695                3700                3705

Glu Glu Val Lys Ser Phe Glu Glu Lys Glu Met Glu Lys Gln Lys
    3710                3715                3720

Leu Leu Tyr Gln Gln Ala Arg Leu His Asp Arg Gly Ala Ala Glu
    3725                3730                3735

Met Val Leu Gln Thr Ile Ser Ala Ser Lys Gly Glu Thr Gly Pro
    3740                3745                3750

Met Val Ala Ala Thr Leu Lys Leu Gly Ile Ala Ile Leu Asn Gly
    3755                3760                3765

Gly Asn Ser Thr Val Gln Gln Lys Met Leu Asp Tyr Leu Lys Glu
    3770                3775                3780

Lys Lys Asp Val Gly Phe Phe Gln Ser Leu Ala Gly Leu Met Gln
    3785                3790                3795

Ser Cys Ser Val Leu Asp Leu Asn Ala Phe Glu Arg Gln Asn Lys
    3800                3805                3810

Ala Glu Gly Leu Gly Met Val Thr Glu Glu Gly Ser Gly Glu Lys
    3815                3820                3825

Val Leu Gln Asp Asp Glu Phe Thr Cys Asp Leu Phe Arg Phe Leu
    3830                3835                3840

Gln Leu Leu Cys Glu Gly His Asn Ser Asp Phe Gln Asn Tyr Leu
    3845                3850                3855

Arg Thr Gln Thr Gly Asn Asn Thr Thr Val Asn Ile Ile Ile Ser
    3860                3865                3870

Thr Val Asp Tyr Leu Leu Arg Val Gln Glu Ser Ile Ser Asp Phe
    3875                3880                3885

Tyr Trp Tyr Tyr Ser Gly Lys Asp Val Ile Asp Glu Gln Gly Gln
    3890                3895                3900

Arg Asn Phe Ser Lys Ala Ile Gln Val Ala Lys Gln Val Phe Asn
    3905                3910                3915
```

```
Thr Leu Thr Glu Tyr Ile Gln Gly Pro Cys Thr Gly Asn Gln Gln
    3920            3925            3930

Ser Leu Ala His Ser Arg Leu Trp Asp Ala Val Val Gly Phe Leu
    3935            3940            3945

His Val Phe Ala His Met Gln Met Lys Leu Ser Gln Asp Ser Ser
    3950            3955            3960

Gln Ile Glu Leu Leu Lys Glu Leu Met Asp Leu Gln Lys Asp Met
    3965            3970            3975

Val Val Met Leu Leu Ser Met Leu Glu Gly Asn Val Val Asn Gly
    3980            3985            3990

Thr Ile Gly Lys Gln Met Val Asp Met Leu Val Glu Ser Ser Asn
    3995            4000            4005

Asn Val Glu Met Ile Leu Lys Phe Phe Asp Met Phe Leu Lys Leu
    4010            4015            4020

Lys Asp Leu Thr Ser Ser Asp Thr Phe Lys Glu Tyr Asp Pro Asp
    4025            4030            4035

Gly Lys Gly Val Ile Ser Lys Arg Asp Phe His Lys Ala Met Glu
    4040            4045            4050

Ser His Lys His Tyr Thr Gln Ser Glu Thr Glu Phe Leu Leu Ser
    4055            4060            4065

Cys Ala Glu Thr Asp Glu Asn Glu Thr Leu Asp Tyr Glu Glu Phe
    4070            4075            4080

Val Lys Arg Phe His Glu Pro Ala Lys Asp Ile Gly Phe Asn Val
    4085            4090            4095

Ala Val Leu Leu Thr Asn Leu Ser Glu His Met Pro Asn Asp Thr
    4100            4105            4110

Arg Leu Gln Thr Phe Leu Glu Leu Ala Glu Ser Val Leu Asn Tyr
    4115            4120            4125

Phe Gln Pro Phe Leu Gly Arg Ile Glu Ile Met Gly Ser Ala Lys
    4130            4135            4140

Arg Ile Glu Arg Val Tyr Phe Glu Ile Ser Glu Ser Ser Arg Thr
    4145            4150            4155

Gln Trp Glu Lys Pro Gln Val Lys Glu Ser Lys Arg Gln Phe Ile
    4160            4165            4170

Phe Asp Val Val Asn Glu Gly Gly Glu Lys Glu Lys Met Glu Leu
    4175            4180            4185

Phe Val Asn Phe Cys Glu Asp Thr Ile Phe Glu Met Gln Leu Ala
    4190            4195            4200

Ala Gln Ile Ser Glu Ser Asp Leu Asn Glu Arg Ser Ala Asn Lys
    4205            4210            4215

Glu Glu Ser Glu Lys Glu Arg Pro Glu Glu Gln Gly Pro Arg Met
    4220            4225            4230

Ala Phe Phe Ser Ile Leu Thr Val Arg Ser Ala Leu Phe Ala Leu
    4235            4240            4245

Arg Tyr Asn Ile Leu Thr Leu Met Arg Met Leu Ser Leu Lys Ser
    4250            4255            4260

Leu Lys Lys Gln Met Lys Lys Val Lys Lys Met Thr Val Lys Asp
    4265            4270            4275

Met Val Thr Ala Phe Phe Ser Ser Tyr Trp Ser Ile Phe Met Thr
    4280            4285            4290

Leu Leu His Phe Val Ala Ser Val Phe Arg Gly Phe Phe Arg Ile
    4295            4300            4305

Ile Cys Ser Leu Leu Leu Gly Gly Ser Leu Val Glu Gly Ala Lys
```

-continued

```
            4310                4315                 4320
Lys Ile Lys Val Ala Glu Leu Leu Ala Asn Met Pro Asp Pro Thr
        4325                4330                 4335
Gln Asp Glu Val Arg Gly Asp Gly Glu Gly Glu Arg Lys Pro
    4340                4345                 4350
Leu Glu Ala Ala Leu Pro Ser Glu Asp Leu Thr Asp Leu Lys Glu
        4355                4360                 4365
Leu Thr Glu Glu Ser Asp Leu Leu Ser Asp Ile Phe Gly Leu Asp
        4370                4375                 4380
Leu Lys Arg Glu Gly Gly Gln Tyr Lys Leu Ile Pro His Asn Pro
        4385                4390                 4395
Asn Ala Gly Leu Ser Asp Leu Met Ser Asn Pro Val Pro Met Pro
        4400                4405                 4410
Glu Val Gln Glu Lys Phe Gln Glu Gln Lys Ala Lys Glu Glu Glu
        4415                4420                 4425
Lys Glu Glu Lys Glu Glu Thr Lys Ser Glu Pro Glu Lys Ala Glu
        4430                4435                 4440
Gly Glu Asp Gly Glu Lys Glu Glu Lys Ala Lys Glu Asp Lys Gly
        4445                4450                 4455
Lys Gln Lys Leu Arg Gln Leu His Thr His Arg Tyr Gly Glu Pro
        4460                4465                 4470
Glu Val Pro Glu Ser Ala Phe Trp Lys Lys Ile Ile Ala Tyr Gln
        4475                4480                 4485
Gln Lys Leu Leu Asn Tyr Phe Ala Arg Asn Phe Tyr Asn Met Arg
        4490                4495                 4500
Met Leu Ala Leu Phe Val Ala Phe Ala Ile Asn Phe Ile Leu Leu
        4505                4510                 4515
Phe Tyr Lys Val Ser Thr Ser Ser Val Val Glu Gly Lys Glu Leu
        4520                4525                 4530
Pro Thr Arg Ser Ser Ser Glu Asn Ala Lys Val Thr Ser Leu Asp
        4535                4540                 4545
Ser Ser Ser His Arg Ile Ile Ala Val His Tyr Val Leu Glu Glu
        4550                4555                 4560
Ser Ser Gly Tyr Met Glu Pro Thr Leu Arg Ile Leu Ala Ile Leu
        4565                4570                 4575
His Thr Val Ile Ser Phe Phe Cys Ile Ile Gly Tyr Tyr Cys Leu
        4580                4585                 4590
Lys Val Pro Leu Val Ile Phe Lys Arg Glu Lys Glu Val Ala Arg
        4595                4600                 4605
Lys Leu Glu Phe Asp Gly Leu Tyr Ile Thr Glu Gln Pro Ser Glu
        4610                4615                 4620
Asp Asp Ile Lys Gly Gln Trp Asp Arg Leu Val Ile Asn Thr Gln
        4625                4630                 4635
Ser Phe Pro Asn Asn Tyr Trp Asp Lys Phe Val Lys Arg Lys Val
        4640                4645                 4650
Met Asp Lys Tyr Gly Glu Phe Tyr Gly Arg Asp Arg Ile Ser Glu
        4655                4660                 4665
Leu Leu Gly Met Asp Lys Ala Ala Leu Asp Phe Ser Asp Ala Arg
        4670                4675                 4680
Glu Lys Lys Lys Pro Lys Lys Asp Ser Ser Leu Ser Ala Val Leu
        4685                4690                 4695
Asn Ser Ile Asp Val Lys Tyr Gln Met Trp Lys Leu Gly Val Val
        4700                4705                 4710
```

```
Phe Thr Asp Asn Ser Phe Leu Tyr Leu Ala Trp Tyr Met Thr Met
    4715                4720                4725

Ser Val Leu Gly His Tyr Asn Asn Phe Phe Ala Ala His Leu
    4730                4735                4740

Leu Asp Ile Ala Met Gly Phe Lys Thr Leu Arg Thr Ile Leu Ser
    4745                4750                4755

Ser Val Thr His Asn Gly Lys Gln Leu Val Leu Thr Val Gly Leu
    4760                4765                4770

Leu Ala Val Val Val Tyr Leu Tyr Thr Val Val Ala Phe Asn Phe
    4775                4780                4785

Phe Arg Lys Phe Tyr Asn Lys Ser Glu Asp Gly Asp Thr Pro Asp
    4790                4795                4800

Met Lys Cys Asp Asp Met Leu Thr Cys Tyr Met Phe His Met Tyr
    4805                4810                4815

Val Gly Val Arg Ala Gly Gly Gly Ile Gly Asp Glu Ile Glu Asp
    4820                4825                4830

Pro Ala Gly Asp Glu Tyr Glu Ile Tyr Arg Ile Ile Phe Asp Ile
    4835                4840                4845

Thr Phe Phe Phe Phe Val Ile Val Ile Leu Leu Ala Ile Ile Gln
    4850                4855                4860

Gly Leu Ile Ile Asp Ala Phe Gly Glu Leu Arg Asp Gln Gln Glu
    4865                4870                4875

Gln Val Lys Glu Asp Met Glu Thr Lys Cys Phe Ile Cys Gly Ile
    4880                4885                4890

Gly Asn Asp Tyr Phe Asp Thr Val Pro His Gly Phe Glu Thr His
    4895                4900                4905

Thr Leu Gln Glu His Asn Leu Ala Asn Tyr Leu Phe Phe Leu Met
    4910                4915                4920

Tyr Leu Ile Asn Lys Asp Glu Thr Glu His Thr Gly Gln Glu Ser
    4925                4930                4935

Tyr Val Trp Lys Met Tyr Gln Glu Arg Cys Trp Glu Phe Phe Pro
    4940                4945                4950

Ala Gly Asp Cys Phe Arg Lys Gln Tyr Glu Asp Gln Leu Asn
    4955                4960                4965
```

<210> SEQ ID NO 2
<211> LENGTH: 14904
<212> TYPE: DNA
<213> ORGANISM: Homo sapiens

<400> SEQUENCE: 2

```
atggccgatg ggggcgaggg cgaagacgag atccagttcc tgcgaactga tgatgaagtg      60
gttctgcagt gcaccgcaac catccacaaa gaacaacaga agctatgctt ggcagcagaa     120
ggatttggca acagactttg tttcttggag tccacttcca attccaagaa tgtgccccca     180
gacctctcca tctgcacctt gtgctggagc agtccctct ctgtccgggc gctgcaggag     240
atgctggcta acaccgtgga gaaatcagaa gggcaagttg atgtggaaaa atggaaattc     300
atgatgaaga ctgctcaagg tggtggtcat cgaacactcc tctacggaca tgccatattg     360
ctgcgccatt cctatagtgg catgtatctg tgctgcctgt ccacctcccg gtcttcaact     420
gataagctgg cttttgatgt tggcttgcaa gaggacacca aggggaggc ttgttggtgg     480 accatacacc ctgcctctaa gcagcgatca gaaggagaaa aagtacgagt tggagatgac     540
ctcatcttag ttagcgtgtc ctctgaaagg tacttgcact tgtcttatgg caacggcagc     600
```

```
ttacacgtgg atgccgcttt ccagcagact ctctggagcg tggccccaat cagctcagga    660
agtgaggcag cccaagggta tctcattggt ggtgatgtcc tcaggttgct gcatggacac    720
atggacgagt gtctcactgt cccttcagga aacatggtg aagagcagcg agaactgtt     780 cattatgaag gtggcgctgt gtctgttcat gcacgttccc tttggagact agagacgcta    840
agagttgcgt ggagtggaag ccacataaga tggggacagc cattccgact acgccatgtc    900
acaacaggaa atacttgag tctcatggaa gacaaaaacc ttctactcat ggacaaagag    960
aaagctgatg taaaatcaac agcatttacc ttccggtctt ccaaggaaaa attggatgta   1020
ggggtgagaa agaagtaga tggcatggga acatctgaaa taaaatacgg tgactcagta   1080
tgctatatac aacatgtaga cacaggccta tggcttactt accagtctgt ggacgtgaaa   1140
tccgtgagaa tgggatctat acaacgtaag gctattatgc atcatgaagg ccacatggat   1200
gatggcataa gtttgtcgag atcccagcat gaagaatcac gcacagcccg agttatccgg   1260
agcacagtct tccttttcaa tagatttata aggggccttg atgctctcag caagaaagcg   1320
aaggcttcca cagtcgattt gcctatagag tccgtaagcc taagtctgca ggatctcatt   1380
ggctacttcc acccccaga tgagcattta gagcatgaag acaaacagaa cagactacga   1440
gccctgaaga atcggcaaaa tctcttccag gaagagggaa tgatcaacct cgtgcttgag   1500
tgcatagacc gtttgcacgt ctacagcagt gcagcacact ttgctgatgt tgctgggcga   1560
gaagcaggag agtcttggaa atccattctg aattctctgt atgagttgct ggcggctcta   1620
attagaggaa atcgtaaaaa ctgtgctcaa tttctggct ccctcgactg gttgatcagc    1680
agattggaaa gactggaagc ttcttcaggc attctggaag ttttacactg tgttttagta   1740
gaaagtccag aagctctaaa tattattaaa gaaggacata ttaaatctat tatctcactt   1800
ttagacaaac atgaagaaa tcacaaggtt ctggatgtct tgtgctcact ctgtgtttgc   1860
cacggggttg cagtccgttc taaccagcat ctcatctgtg acaatctcct accaggaaga   1920
gacttgttat tgcagacacg tcttgtgaac catgtcagca gcatgagacc caatattttt   1980
ctgggcgtca gtgaaggttc tgctcagtat aagaaatggt actatgaatt gatggtggac   2040
cacacagagc cctttgtgac agctgaagca actcacctgc gagtgggctg ggcttccact   2100
gaaggatatt ctccctaccc tggaggggc gaagagtggg gtggaaatgg tgttggagat   2160
gatctcttct cctatggatt tgatggcctt catctctggt caggttgtat tgctcgtact   2220
gtaagctcac caaaccaaca tctgttaaga actgatgatg tcatcagttg ctgtttagat   2280
ctgagtgccc caagcatctc gttccgaatt aatggacaac ctgttcaagg aatgtttgag   2340
aatttcaaca tcgatggcct cttctttcca gtcgttagtt tctctgcagg aataaaagta   2400
cgctttctgc ttggagggcg acatggagaa ttcaaatttc ttcctccacc tgggtatgct   2460
ccttgttatg aagctgttct gccaaaagaa aagttgaaag tggaacacag ccgagagtac   2520
aagcaagaaa gaacttacac acgcgacctg ctgggcccca gtttccct gacgcaagct    2580 gccttcacac ccatccctgt ggataccagc cagatcgtgt tgcctcctca tctagaaaga   2640
ataagagaaa aactggcaga gaatatccat gaactctggg ttatgaataa aattgagctt   2700
ggctggcagt atggtccggt tagagatgac aacaagagac aacacccatg cctggtggag   2760
ttctccaagc tgcctgaaca ggagcgcaat tacaacttac aaatgtcgct tgagaccctg   2820
aagactttgt tggcattagg atgtcatgtg ggtatatcag atgaacatgc tgaagacaag   2880 gtgaaaaaa tgaagctacc caagaattac cagctgacaa gtggatacaa gcctgcccct   2940
```

```
atggacctga gctttatcaa actcacccca tcgcaagaag caatggtgga caagttggca    3000
gaaaatgcac ataatgtgtg ggcgcgggat cgaatccggc agggctggac ttatggcatc    3060
caacaggacg taaagaacag aagaaatcct cgccttgttc cctacactcc tctggatgac    3120
cgaaccaaga atccaacaa ggacagcctc cgcgaggctg tgcgcacgct gctggggtac     3180
ggctacaact tggaagcacc agatcaagat catgcagcca gagccgaagt gtgcagcggc    3240
accggggaaa ggttccgaat cttccgtgcc gagaagacct atgcagtgaa ggccggacgg    3300
tggtattttg aatttgagac ggtcactgct ggagacatga gggttggttg gagtcgtcct   3360
ggttgtcaac cggatcagga gcttggctca gatgaacgtg cctttgcctt tgatggcttc   3420
aaggcccagc ggtggcatca gggcaatgaa cactatgggc gctcttggca agcaggcgat   3480
gtcgtggggt gtatggttga catgaacgaa cacaccatga tgttcacact gaatggtgaa   3540
atccttcttg atgattcagg ctcagaactg gctttcaagg actttgatgt tggcgatgga   3600
ttcatacctg tgtgtagcct tggagtggct caagtgggta ggatgaactt tggaaaggat   3660
gtcagcacct tgaaatattt caccatctgt ggcttacaag agggctatga accatttgcc   3720
gttaatacaa acagggatat taccatgtgg ctgagcaaga ggcttcctca gtttcttcaa   3780
gttccatcaa accatgaaca tatagaggtg accagaatag acggcaccat agacagttcc   3840
ccatgtttaa aggtcactca gaagtctttt ggttctcaga acagcaacac tgatatcatg   3900
ttttatcgcc tgagcatgcc gatcgagtgc gcggaggtct ctccaagac ggtggctgga    3960
gggctccctg gggctggcct ttttgggccc aagaatgact tggaagatta tgatgctgat   4020
tctgactttg aggttctgat gaagacagct catggccatc tagtgcccga tcgtgttgac   4080
aaagacaaag aagctactaa accagagttt aacaaccaca agattatgc ccaggaaaag    4140
ccctctcgtc tgaaacaaag attttttgctt agaagaacaa agccagatta cagcacaagc   4200
cattctgcaa gactcaccga agatgtcctt gctgatgatc gggatgacta tgatttcttg   4260
atgcaaacgt ccacgtacta ttactcagtg agaatctttc ctggacaaga acctgctaat   4320
gtctgggtgg gctggattac atcagatttc catcagtatg acacaggctt tgacttggac   4380
agagttcgca cagtaacagt tactctagga gatgaaaaag gaaaagtgca tgaaagcatc   4440
aaacgcagca actgctatat ggtatgtgcg ggtgagagca tgagccccgg gcaaggacgc   4500
aacaataatg gactggagat tggctgtgtg gtggatgctg ccagcgggct gctcacattc   4560
attgccaatg gcaaggaact gagcacatac tatcaggtgg aaccgagtac aaaattattt   4620
cctgcggttt ttgcacaagc tacaagtccc aatgttttcc agtttgagtt gggaagaata   4680
aagaatgtga tgcctctctc ggcgggatta ttcaagagtg agcacaagaa ccccgtgccg   4740
cagtgccccc cgcgcctcca cgtgcagttc ctgtcacacg tcctgtggag cagaatgccc   4800
aaccagtttt tgaaggtaga tgtgtctcga ataagtgaac gccaaggctg gttggtgcag   4860
tgtttggatc ctctgcagtt catgtctctt catatccctg aggaaaacag atctgttgac   4920
atcttagagt tgacagagca ggaggaattg ctgaaatttc actatcacac tctccggctc   4980
tactcagccg tctgtgctct tgggaaccac cgggtggccc atgccctgtg cagccatgtg   5040
gatgaacctc agctcctcta tgccattgag aacaagtaca tgcctggttt gctgcgtgct   5100
ggctactatg acctgctgat tgacatccac ctgagctcct atgccactgc aggctcatg    5160
atgaacaacg agtacattgt ccccatgacg gaggagacga gagcatcac cctgttccct    5220
gatgagaaca aaaacacgg ccttccaggg atcggcctca gcacctccct caggccacgg     5280
atgcagtttt cctcccccag ttttgtaagc attagtaatg aatgttacca gtacagtcca   5340
```

```
gagttcccac tggacatcct caagtccaaa accatacaga tgctgacaga agctgttaaa   5400
gagggcagtc ttcatgcccg ggacccagtt ggagggacta ctgaattcct ctttgtacct   5460
ctcatcaagc ttttctatac cctgctgatc atgggcatct ttcacaacga ggacttgaag   5520
cacatcttgc agttgattga gcccagtgtg tttaaagaag ctgccactcc ggaggaggag   5580
agtgacacgc tggagaaaga gctcagtgtg gacgatgcaa agctgcaagg agctggtgag   5640
gaagaagcca aggggggcaa gcggcccaag gaaggcctgc tccaaatgaa actgccagag   5700
ccagttaaat tgcagatgtg cctactgctt cagtacctct gtgactgcca ggtccggcac   5760
cggatagaag ccattgtagc cttttcagat gattttgtgg ctaagctcca agacaatcaa   5820
cgtttccgat acaacgaagt catgcaagcc ttaaacatgt cagctgcact cacagccagg   5880
aagacaaagg aatttagatc accacctcaa gaacagatca atatgcttct caattttaag   5940
gatgacaaaa gtgaatgtcc atgtccagaa gaaattcgtg accaactatt ggatttccat   6000
gaagatttga tgacacattg tggaattgag ctggatgaag atgggtctct ggatggaaac   6060
agtgatttaa caattagagg gcgtctgcta tccctggtag aaaaggtgac atatctgaag   6120
aagaagcaag cagaaaaacc agttgagagt gactccaaaa agtcctccac tctgcagcag   6180
ctgatttctg agaccatggt ccgatgggct caggagtctg tcattgaaga ccccgagctg   6240
gtgagggcca tgtttgtgtt gctccatcgg cagtatgacg gcattggggg tcttgttcgg   6300
gccctgccaa agacctacac gataaatggt gtgtccgtgg aggacaccat caacctgctg   6360
gcatcccttg gtcagattcg gtccctgctg agtgtgagaa tggcaaagaa agaagagaag   6420
ctcatgattc gtggattagg ggatattatg aataacaaag tgttttacca gcaccctaat   6480
ctcatgaggg cactggggat gcacgagact gtgatggagg tcatggtgaa cgtccttgga   6540
ggtggagagt ccaaggaaat cacctttccc aagatggtgg ccaactgttg ccgttttctc   6600
tgttacttct gtcgtataag taggcagaat caaaaagcta tgtttgatca tctcagttat   6660
ttactggaaa acagcagtgt tggtcttgcc tccccagcta tgagaggttc aacaccactg   6720
gatgtggctg cagcttcggt gatggataat aatgaactag cattagctct gcgtgagccg   6780
gatctagaaa aggtagttcg ttatttggct ggttgtggac tgcaaagttg ccagatgctg   6840
gtgtctaagg gctatccaga cattgggtgg aacccagttg aaggagagag atatcttgac   6900
tttctcagat ttgctgtctt ctgtaatggg gagagtgtgg aggaaaatgc aaatgtcgtg   6960
gtgagattgc tcattcggag gcctgagtgt tttggtcctg ctttgagagg agaaggtggg   7020
aatgggcttc ttgcagcaat ggaagaagcc atcaaaatcg ccgaggatcc ttcccgagat   7080
ggtccctcac caaatagcgg atccagtaaa acacttgaca cagaggagga ggaagatgac   7140
actatccaca tggggaacgc gatcatgacc ttctattcag ctttgattga cctcttggga   7200
cgctgtgctc ctgagatgca tttgattcat gccgggaagg agaagccat cagaattagg   7260
tccattttga gatccctcat tcccctggga gatttggtgg gcgttatcag catcgctttt   7320
cagatgccaa caatagccaa agatgggaat gtggtggaac ctgacatgtc tgcgggggtt   7380
tgcccagatc acaaggcagc catggttttta ttccttgaca gggtctatgg gattgaggtt   7440
caagacttcc tcctccatct tcttgaggtt ggctttctgc agatctccgg gcggctgct   7500
tctttagata cggcagcttt gagtgctaca gacatggcct tggccctcaa tcggtacctt   7560
tgcacagccg tcttgccatt gttaacaaga tgtgctcctc tctttgctgg cacagagcac   7620
cacgcttctc tcattgactc attacttcat actgtgtata gactttctaa gggctgttca   7680
```

```
cttaccaaag ctcagcggga ttccatagaa gtttgtttac tctctatttg tggacaactg    7740
agaccttcta tgatgcagca cttactcaga agattagtat ttgatgtccc attattaaat    7800
gaacacgcaa agatgcctct taaactgctg acaaatcatt atgaaagatg ctggaaatat    7860
tactgcctgc ctggagggtg gggaaacttt ggtgctgcct cagaagaaga acttcattta    7920
tcaagaaagt tgttctgggg cattttttgat gccctgtctc aaaagaaata tgaacaagaa    7980
cttttcaaac tggcactgcc ttgcctgagt gcagttgcgg gagctttgcc tccagactac    8040
atggagtcaa attatgtcag tatgatggaa aaacagtcat caatggattc tgaagggaac    8100
tttaacccac aacctgttga tacctcaaat attacaattc ctgagaaatt ggaatacttc    8160
attaacaaat atgcagaaca ctcccatgac aaatggtcaa tggacaagtt ggcaaatgga    8220
tggatttatg agaaaatata ttcagactct tctaaggttc agccattaat gaagccatat    8280
aagctattgt ctgaaaagga aaaagaaatt tatcgctggc caatcaaaga atctttaaaa    8340
actatgctgg ctaggactat gagaactgaa agaactcggg agggagacag catggccctt    8400
tacaaccgga ctcgtcgtat ttctcagaca agccaggttt ctgtggacgc tgcccatggt    8460
tacagtcccc gggccattga catgagcaat gttacactat ctagagacct gcatgctatg    8520
gcagaaatga tggctgaaaa ctaccataat atatgggcaa agaaaaagaa aatggagttg    8580
gagtccaaag gaggaggaaa ccatcctctg ctggtgccct atgatacact gacagccaaa    8640
gagaaagcca aggatagaga aaaagcacag gacatcctca agttcttgca gatcaatgga    8700
tatgctgtat ccagaggatt taaggacctg gaactggaca cgccttctat tgagaaacga    8760
tttgcctata gtttcctcca acaactcatt cgctatgtgg atgaagccca tcagtatatc    8820
ctggagtttg atggtggcag cagaggcaaa ggagaacatt tcccttatga acaagaaatc    8880
aagttctttg caaaagtcgt tcttcctta attgatcagt atttcaaaaa ccatcgttta    8940
tacttcttat ctgcagcaag cagacctctc tgctctggag acatgcttc caacaaagag    9000 aaagaaatgg tgactagcct attctgcaaa cttggagttc ttgtcaggca taggatttca    9060
ctatttggca atgatgcaac atcaattgtc aactgtcttc atattttggg tcagactttg    9120
gatgcaagga cagtgatgaa gactggcctg gagagtgtta aaagtgcact cagagctttt    9180
ctggacaacg ctgcagagga tctggagaag accatggaaa acctcaagca gggccagttc    9240
actcacaccc gaaaccagcc caagggggtt actcagatta tcaattacac cacagtggcc    9300
ctgctgccaa tgctgtcgtc attatttgaa catattggcc agcatcagtt cggagaagac    9360
ctaatattgg aagatgtcca ggtgtcttgt tatagaattc tgactagctt atatgctttg    9420
ggaaccagca agagtattta cgtggagagg caacgttctg cattaggaga atgtctagct    9480
gcctttgctg gtgcttttcc tgtagcattt ttggaaactc atctgacaa acataatatt    9540 tactccatct acaataccaa gtcttcacga gaaagagcag ctctcagttt gccaactaat    9600
gtggaagatg tttgtccaaa cattccgtct ttggagaaac tcatgaaga aatcgtggaa    9660 ttagccgagt ccggcattcg ctacactcaa atgccacatg tcatggaagt catactgccc    9720
atgctttgca gctacatgtc tcgttggtgg agcatggac ctgagaacaa tccagaacgg    9780
gccgagatgt gctgcacagc cctgaactca gagcacatga acacacttct agggaacata    9840
ttgaaaatca tatataataa cttggggatt gatgagggag cctggatgaa gaggctagca    9900 gtgtttttccc agcctataat aaataaagtg aaacctcagc tcttgaaaac tcatttcttg    9960
ccgttaatga agaaactcaa gaaaaaggca gctacggtgg tgtctgagga agaccacctg   10020
aaagctgagg ccaggggga catgtcggag gcagaactcc tcatcctaga tgagttcacc   10080
```

```
acactggcca gagatctcta tgccttctac cctctcttga ttagatttgt ggactataac    10140
agggcaaagt ggctaaagga gcctaaccca gaagcagagg agctcttccg catggtggct    10200
gaagtgttta tctactggtc gaagtcccat aatttcaaaa gagaagagca gaacttcgtt    10260
gtacagaatg aaatcaacaa tatgtctttc cttattactg ataccaagtc aaagatgtca    10320
aaggcagctg tttctgatca ggaaaggaag aaaatgaagc gcaaaggaga tcggtattcc    10380
atgcagacct ctctgattgt agcagctctg aagcggttac tgcccattgg gttgaacatc    10440
tgtgcccctg ggaccagga gctcattgct ctggccaaaa atcgatttag cctgaaagat    10500
actgaggatg aagtacgaga tataatccgc agcaatattc atttacaagg caagttggag    10560
gatcctgcta ttagatggca aatggctctt tacaaagact taccaaacag gactgatgat    10620
acctcagatc cagagaagac ggtagaaaga gtattggata tagcaaatgt gcttttttcat    10680 cttgaacaga agtctaaacg tgtgggtcga agacattact gtctggtgga acatcctcag    10740
agatctaaaa aggctgtatg gcataaacta ctgtctaagc agaggaaaag ggctgttgta    10800
gcctgcttcc ggatggcccc cttatataat ctgccaaggc atcgggctgt caatctcttt    10860
cttcagggat atgaaaagtc ttggattgaa acagaagaac attactttga agataaactg    10920
atagaagatt tagcaaaacc tggggctgaa cctccagaag aagatgaagg cactaagaga    10980
gttgatcctc tacatcagct gatccttctg tttagtcgga cagctttaac agagaaatgc    11040
aaactggagg aagatttttt atatatggcc tatgcagata ttatggcaaa gagttgtcat    11100
gatgaggaag atgacgatgg tgaagaggaa gtgaagagtt ttgaagaaaa agaaatggaa    11160
aagcaaaagc ttctatacca gcaagcccga ctccacgatc gtggcgcggc tgagatggtg    11220
ctacagacaa tcagtgccag caaaggtgaa actggaccaa tggtagcagc tactctgaaa    11280
cttggaattg ctatttttaaa tggtgggaac tccacagtac agcagaaaat gcttgactac    11340
ctcaaggaga aaaaggatgt gggcttcttt cagagcctgg ccggcctgat gcagtcatgt    11400
agtgtccttg acctaaatgc atttgagcga caaaacaaag ctgaaggtct tgggatggtg    11460
acagaggaag atcaggaga aaaggttctg caggacgatg agttcacctg tgacctcttc    11520
cgattcctgc aactactctg tgagggacac aactcagatt ttcagaatta tctgagaact    11580
cagactggca ataatacaac tgtcaacata attatctcca ctgtagacta cctactgaga    11640
gttcaggaat caattagtga ctttttattgg tattactctg ggaaagatgt tattgatgaa    11700
caaggacaac ggaatttctc caaagctatc caagtggcaa aacaagtctt taacactctt    11760
acagagtata ttcagggtcc ttgcactggg aatcaacaga gtttggcaca cagcaggctg    11820
tgggatgctg tggtcggctt tcttcatgtg tttgcccata tgcagatgaa gctgtcgcag    11880
gattccagtc aaattgagct attaaaagaa ttaatggatc tgcagaagga tatggtggtc    11940
atgttgctgt ccatgttaga aggtaatgtt gttaatggaa cgattggcaa acagatggtg    12000
gatatgcttg tggaatcttc caacaacgtg gagatgattc tcaaattttt tgacatgttc    12060
ttaaaactaa aggatttgac gtcgtctgat acttttaaag aatatgaccc cgatggcaag    12120
ggagtcattt ccaagaggga cttccacaaa gcgatggaga gccataagca ctacacgcag    12180
tcagaaacgg aatttctttt gtcttgtgcg gagacggatg agaatgaaac cctcgactac    12240
gaagagttcg tcaaacgctt ccacgaacct gcgaaggaca tcggcttcaa cgtcgccgtc    12300
cttctgacaa acctctctga gcacatgccc aacgataccc gacttcagac ttttctggaa    12360
ttagcagaga gcgtcctgaa ttatttccag cccttttctgg gccgcatcga aatcatggga    12420
```

```
agcgccaaac gcatcgagag ggtctatttt gaaatcagtg agtccagccg aacccagtgg    12480
gagaagcccc aggtcaagga gtccaaaaga cagttcatat ttgacgtggt caacgaaggc    12540
ggagagaaag agaagatgga actctttgtg aacttctgcg aggacaccat ctttgaaatg    12600
cagctggcgg ctcagatctc ggagtcggac ttgaacgaga ggtcagcgaa taaggaagaa    12660
agcgagaagg agaggccgga agagcagggg ccgaggatgg ctttcttctc cattctgacg    12720
gtcaggtcgg ccctgtttgc gctcaggtac aatatcttga cccttatgcg aatgctcagt    12780
ctgaagagcc tgaagaagca gatgaaaaaa gtaaaaaaga tgaccgtgaa ggacatggtc    12840
acggccttct tttcatccta ctggagtatt ttcatgaccc tcttgcactt cgtggccagc    12900
gttttcagag gcttttttccg catcatttgc agcctgctgc ttgggggaag cctcgtcgaa    12960
ggtgctaaaa agatcaaagt tgcagaactg ttagccaaca tgccagaccc cactcaggat    13020
gaggttagag gagatgggga ggagggagag aggaaacccc tggaagccgc cctgccctcc    13080
gaggatctga ccgacttaaa ggagctgaca gaggaaagtg accttctttc ggacatcttt    13140
ggcctggatc tgaagagaga aggaggacag tacaaactga ttcctcataa tccaaatgct    13200
gggctcagtg acctcatgag caacccagtc cccatgcctg aggtgcagga aaaatttcag    13260
gaacagaagg caaaagaaga agaaaaggaa gaaaaagaag aaaccaaatc tgaacctgaa    13320
aaagccgagg gagaagatgg agaaaaagaa gagaaagcca aggaagacaa gggcaaacaa    13380
aagttgaggc agcttcacac acacagatac ggagaaccag aagtgccaga gtcagcattc    13440
tggaagaaaa tcatagcata tcaacagaaa cttctaaaact attttgctcg caacttttac    13500
aacatgagaa tgttagcctt atttgtcgca tttgctatca atttcatctt gctctttttat    13560 aaggtctcca cttcttctgt ggttgaagga aaggagctcc ccacgagaag ttcaagtgaa    13620
aatgccaaag tgacaagcct ggacagcagc tcccatagaa tcatcgcagt tcactatgta    13680
ctagaggaga gcagcggcta catggagccc acgttgcgta tcttagctat tctgcacacg    13740
gtcatttctt tcttctgcat cattggatac tactgcttga aagtcccatt ggttattttt    13800
aagcgagaaa aggaagtggc acggaaattg gaatttgatg gctttatat tacagaacag    13860 ccttcagaag atgatattaa aggccagtgg gatagactcg taatcaacac acagtcattt    13920
cccaacaact actgggacaa atttgttaaa agaaaggtta tggataaaata tggagagttc    13980 tacggccgag acagaatcag tgaattactt ggcatggaca aggcagctct ggacttcagt    14040
gatgccagag aaaagaagaa gccaaagaaa gacagctcct tatcagctgt actgaactcc    14100
attgatgtga agtatcagat gtggaaacta ggagtcgttt tcactgacaa ctccttcctc    14160
tacctagcct ggtatatgac tatgtctgtt cttggacact ataacaactt ttttttttgcc    14220 gctcaccttc tcgacattgc tatgggattc aagacattaa gaaccatctt gtcctcagta    14280
actcacaatg gcaaacagct cgtattaacc gttggcttat tagctgttgt tgtataccta    14340
tacactgtgg tggcattcaa ttttttccga aaattctaca ataaaagtga agatggtgat    14400
acaccagata tgaaatgtga cgatatgcta acatgctata tgttccacat gtatgttgga    14460
gttcgtgctg gaggagggat cggggatgaa atcgaagacc agcaggaga tgaatatgag    14520 atctatcgaa tcatctttga catcactttc ttcttctttg ttattgtcat tctcttggcc    14580
ataatacaag gtctaattat tgatgctttt ggagaactaa gagaccaaca ggaacaagtc    14640
aaagaagaca tggagaccaa atgcttcatc tgtgggatag gcaatgatta cttcgacaca    14700
gtgccacatg gctttgaaac ccacactttta caggagcaca acttggctaa ttacttgttt    14760
tttctgatgt atcttataaa caaagatgaa acagaacaca caggacagga atcttatgtc    14820
```
tggaagatgt atcaagaaag gtgttgggaa ttttcccag cagggattg cttccggaaa    14880 cagtatgaag accagctaaa ttaa                                          14904

```
<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

Glu Asp Thr Ile Asn Leu Leu Ala Ser Leu Gly Gln Ile Arg Ser Leu
1               5                   10                  15

Leu Ser Val Arg Met Gly Lys Glu Glu Glu Lys Leu Met Ile Arg Gly
            20                  25                  30

Leu Gly Asp Ile
        35

```
<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

Met Ser Val Glu Asp Thr Ile Asn Leu Leu Ala Ser Leu Gly Gln Ile
1               5                   10                  15

Arg Ser Leu Leu Ser Val Arg Met Gly Lys Glu Glu Glu Lys Leu Met
            20                  25                  30

Ile Arg Gly Leu Gly Asp Ile
        35

```
<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

Glu Asp Thr Ile Asn Leu Leu Ala Ser Leu Gly Gln Ile Arg Ser Leu
1               5                   10                  15

Leu Ser Val Arg Met Gly Lys Glu Glu Glu Lys Leu Met Ile
            20                  25                  30

```
<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6
```

Glu Asp Thr Ile Asn Leu Leu Ala Ser Leu Gly Gln Ile Arg Ser Leu
1               5                   10                  15

Leu Ser Val Arg Met Gly Lys Glu Glu
            20                  25

```
<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Asp Thr Ile Asn Leu Leu Ala Ser Leu Gly Gln Ile Arg Ser Leu
1               5                   10                  15

Leu Ser Val Arg
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Arg Ser Leu Leu Ser Val Arg Met Gly Lys Glu Glu Glu Lys Leu
1               5                   10                  15

Met Ile Arg Gly
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Ser Val Arg Met Gly Lys Glu Glu Glu Lys Leu Met Ile Arg Gly
1               5                   10                  15

Leu Gly Asp Ile
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Val Ser Leu Leu Ser Arg Ile Gln Gly Leu Ser Ala Leu Leu Asn
1               5                   10                  15

Ile Thr Asp Glu
            20

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

```
Glu Asp Thr Ile Asn Leu Leu Ala Ser Leu
1               5                   10
```

```
<210> SEQ ID NO 12
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

```
Glu Asp Thr Ile Asn Leu Leu Ala Ser Leu Gly Gln Ile Arg Ser Leu
1               5                   10                  15

Leu Ser Met Arg Met Gly Lys Glu Glu Lys Leu Met Ile Arg Gly
            20                  25                  30

Leu Gly Asp Ile
            35
```

```
<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

```
Arg Trp Ala Gln Glu Ser Val Ile Glu Asp Pro Glu Leu Val Arg Ala
1               5                   10                  15

Met Phe Val Leu
            20
```

```
<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

```
Val Leu Leu His Arg Gln Tyr Asp Gly Ile Gly Gly Leu Val Arg Ala
1               5                   10                  15

Leu Pro Lys Thr Tyr Thr Ile Asn Gly Val Ser Val
            20                  25
```

```
<210> SEQ ID NO 15
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Val Leu Leu His Arg Gln Tyr Asp Gly Ile Gly Gly Leu Val Arg Ala
1               5                   10                  15

Leu Pro Lys Thr Tyr Thr Ile Asn Gly Val Ser Val Glu Asp Thr Ile
            20                  25                  30

Asn Leu Leu Ala Ser Leu Gly Gln Ile Arg Ser Leu Leu Ser Val Arg
        35                  40                  45
```

```
<210> SEQ ID NO 16
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Asn Asn Lys Val Phe Tyr Gln His Pro Asn Leu Met Arg Ala Leu
1               5                   10                  15

Gly Met His Glu Thr Val Met Glu Val Met Val Asn Val Leu Gly Gly
            20                  25                  30

Gly Glu Ser Lys
            35

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Glu Ala Ala Thr Pro Glu Glu Ser Asp Thr Leu Glu Lys Glu
1               5                   10                  15

Leu Ser Val Asp
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Asp Thr Leu Glu Lys Glu Leu Ser Val Asp Asp Ala Lys Leu Gln
1               5                   10                  15

Gly Ala Gly Glu
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Asp Ala Lys Leu Gln Gly Ala Gly Glu Glu Glu Ala Lys Gly Gly
1               5                   10                  15

Lys Arg Pro Lys
            20

<210> SEQ ID NO 20
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
```

```
gaggacacca tcaacctgct ggcatcccct ggtcagattc ggtccctgct gagtgtgaga      60
atgggcaaag aagaagagaa gctcatgatt cgtggattag gggatatt                 108

<210> SEQ ID NO 21
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgtccgtgg aggacaccat caacctgctg gcatcccttg gtcagattcg gtccctgctg      60
agtgtgagaa tgggcaaaga agaagagaag ctcatgattc gtggattagg ggatatt        117

<210> SEQ ID NO 22
<211> LENGTH: 90
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gaggacacca tcaacctgct ggcatcccct ggtcagattc ggtccctgct gagtgtgaga      60
atgggcaaag aagaagagaa gctcatgatt                                      90

<210> SEQ ID NO 23
<211> LENGTH: 75
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gaggacacca tcaacctgct ggcatcccct ggtcagattc ggtccctgct gagtgtgaga      60
atgggcaaag aagaa                                                      75

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gaggacacca tcaacctgct ggcatcccct ggtcagattc ggtccctgct gagtgtgaga      60

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
attcggtccc tgctgagtgt gagaatgggc aaagaagaag agaagctcat gattcgtgga      60

<210> SEQ ID NO 26
<211> LENGTH: 60
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ctgagtgtga gaatgggcaa agaagaagag aagctcatga ttcgtggatt aggggatatt      60
```